United States Patent
García Suero et al.

(10) Patent No.: US 10,676,427 B2
(45) Date of Patent: Jun. 9, 2020

(54) DIAZOMETHYLATION REAGENT AND PROCESS FOR USING IT

(71) Applicant: FUNDACIÓ INSTITUT CATALÀ D'INVESTIGACIÓ QUÍMICA (ICIQ), Tarragona (ES)

(72) Inventors: Marcos García Suero, Tarragona (ES); Zhaofeng Wang, Tarragona (ES)

(73) Assignee: FUNDACIÓ INSTITUT CATALÀ D'INVESTIGACIÓ QUÍMICA (ICIQ), Tarragona (ES)

( * ) Notice: Subject to any disclaimer, the term of this patent is extended or adjusted under 35 U.S.C. 154(b) by 0 days.

(21) Appl. No.: 16/482,966

(22) PCT Filed: Feb. 8, 2018

(86) PCT No.: PCT/EP2018/053190
§ 371 (c)(1),
(2) Date: Aug. 1, 2019

(87) PCT Pub. No.: WO2018/146200
PCT Pub. Date: Aug. 16, 2018

(65) Prior Publication Data
US 2020/0010409 A1 Jan. 9, 2020

(30) Foreign Application Priority Data
Feb. 9, 2017 (EP) .................... 17382063

(51) Int. Cl.
C07C 271/26 (2006.01)
C07C 245/18 (2006.01)
C07C 251/00 (2006.01)
C07D 347/00 (2006.01)
C07B 47/00 (2006.01)

(52) U.S. Cl.
CPC .......... *C07C 271/26* (2013.01); *C07C 245/18* (2013.01); *C07C 251/00* (2013.01); *C07D 347/00* (2013.01); *C07B 47/00* (2013.01)

(58) Field of Classification Search
CPC ... C07C 271/26; C07C 245/18; C07C 251/00; C07D 347/00; C07B 47/00
See application file for complete search history.

(56) References Cited

PUBLICATIONS

Li et al., Cyclic Hypervalent Iodine Reagents for Atom-Transfer Reactions: Beyond Trifluoronnethylation, 55(14) Angewandte Chemie Int'l Ed., 4436-4454 (2016) (Year: 2016).*
International Search Report and Written Opinion dated Apr. 26, 2018 for PCT Application No. PCT/EP2018/053190, 12 pages.
Cernak, et al: "The medicinal chemist's toolbox for late stage functionalization of drug-like molecules", Chem Soc Rev 2015, vol. 45, pp. 546-576.
Ford, et al: "Modern organic synthesis with a-Diazocarbonyl Compounds", Chemical Reviews 2015, vol. 115, pp. 9981-10080.
Li et al: "Cyclic hypervalent iodine reagents for atom-transfer reactions: Beyond Trifluoromethylation", J. Angew. Chem. Int. Ed., 2016, vol. 55, pp. 4436-4454.
Schnaars, et al: "Nucleophilic halogenations of Diazo compounds, a complementary principle for the synthesis of halodiazo compounds: experimental and theoretical studies", Jounal of Organic Chemistry, Jul. 2, 2013, vol. 78, pp. 7488-7497.
Weiss, et al: "x-Aryliodonio Diazo Compounds: SN Reactions at the x-C atom as a novel reaction type for diazo compounds", J. Angew. Chem. Int. Ed. Engl., 1994, vol. 33, No. 19, pp. 1952-1953.

* cited by examiner

*Primary Examiner* — Timothy R Rozof
(74) *Attorney, Agent, or Firm* — Squire Patton Boggs (US) LLP

(57) ABSTRACT

The present invention relates compounds useful as reagents for the diazomethylation reaction, their preparation and the use thereof as reagents in a method for the diazomethylation reaction of aromatic substrates. It relates in particular to a compound of formula (I) wherein E is an electron withdrawing group.

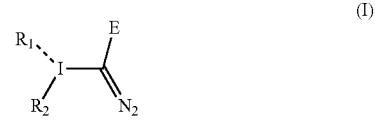

20 Claims, No Drawings

DIAZOMETHYLATION REAGENT AND PROCESS FOR USING IT

This application claims the benefit of European Patent Application EP17382063.0 filed on Feb. 2, 2017.

The present invention relates to a compound useful as diazomethylation reagent and to a method for the diazomethylation of aromatic substrates. It also relates to a method for its preparation and the use thereof as a reagent.

BACKGROUND ART

Medicinal chemists are constantly seeking and developing synthetic procedures for the introduction of functional groups into compounds showing potential biological activity in order to fine-tune the properties of said compounds. For instance, it has been shown that the introduction of a trifluoromethyl group into the scaffold of a biologically active compound tends to enhance the biological activity of the same, which in turn, leads to the development of several synthetic methodologies and reagents for the introduction of the trifluoromethyl group in the last synthetic step. In the same manner, the introduction of labelled atoms into existing compounds, such as $^{11}$C or $^{18}$F, allows preparing radiotracers for applications in medical imaging (Positron Emission Tomography). In both cases, suitable synthetic methods and reagents are required for the introduction of functional groups of interest into a molecular scaffold. Currently, late-stage functionalization approaches, as those reviewed by Cernak and co-workers have been developed for the introduction of various functional groups, for example into aromatic C—H bonds.

On the other hand, the radicals derived from the diazomethyl group, such as 1-diazo-2-alkyloxy-2-oxoethyl or 1-diazo-2,2,2-trifluoroethyl, represent a highly versatile functional group, since the diazo functionality represents a carbene precursor. Such functional groups are commonly found in starting materials for a broad number of chemical reactions such as cyclopropanation, cycloaddition, oxidation, amination, halogenation, arylation and epoxidation among others, as described for instance in Ford et al. The diazomethyl functional group therefore represents a good starting point in the preparation of compounds with high molecular diversity from one sole starting material, making it suitable for applications in the discovery and development of biologically active molecules, such as agrochemicals and drugs.

However, the introduction of a diazomethyl group into an aromatic C—H bond in one sole synthetic step has not yet been reported. Several methods have been reported in the state of the art for the introduction of a diazomethyl group into an aromatic C—H bond. Such methods are multi-step sequences, and usually involve a Friedel-Crafts acylation reaction (preparation of aryl ketones from aromatic substrates and acid chlorides), followed by a treatment with hydrazine and subsequent transformation of the resulting hydrazone compound to the desired diazomethyl derivative. This multi-step synthetic sequence typically requires using harsh conditions of reaction and unstable or sensitive reagents (such as hydrazine, Lewis acids or hydrazone oxidizing agent), making it unsuitable for highly functionalized starting materials and late-stage functionalization approach.

Furthermore, several hypervalent diazomethyliodine compounds have been reported in the literature. Schnaars et al. reported a series of alpha-aryl iodonio diazo derivatives and their use as sources of diazomethyl groups in nucleophilic substitution reactions, in particular in the preparation of halogenated diazomethyl derivatives. Furthermore, Weiss et al. described similar reagents for use as electrophiles in nucleophilic substitution reactions. The use of these compounds in reactions of functionalization of aromatic C—H bonds comprised in a reaction substrate has however not been reported. The reported alpha-aryl iodonio diazo derivatives have the following formulae:

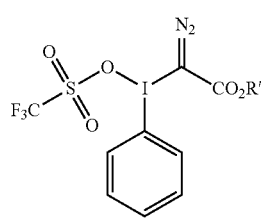

(Ia)

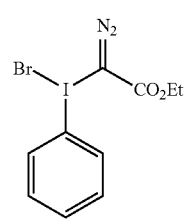

(Ib)

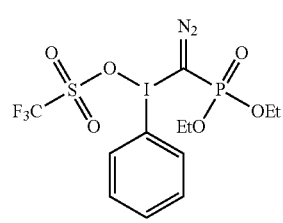

(Ic)

where R' is ethyl or tert-butyl. In both cases, these compounds are used in reaction with substrates comprising a nucleophilic heteroatom which attacks the carbon atom of the diazomethyl iodine derivative to form a product wherein the diazomethyl radical is linked to the aforementioned heteroatom.

Furthermore, Li et al. also review the use of benzoiodoxolone reagents in the formation of C—C bond. The authors are silent about the use of these compounds in the diazomethylation of aromatic C—H bonds.

Thus, even though several synthetic tools have been reported for late-stage functionalization of organic compounds and for the insertion of diazomethyl radicals into aromatic C—H bonds, there is still the need for methods and reagents for the insertion of diazomethyl groups into aromatic C—H bonds that is carried out in one synthetic step and in mild conditions, and that exhibits high functional group tolerance.

SUMMARY OF THE INVENTION

The inventors have found that, when treating an aromatic substrate with an alpha-aryl iodonio diazomethyl derivative in the presence of a reducing agent, a diazomethyl radical is readily incorporated into an aromatic C—H bond comprised in the substrate. This process advantageously takes place in one sole synthetic step and in mild conditions. The inventors have also found new compounds useful as reagents for this transformation.

Without being bound to theory, it is believed that the treatment of the alpha-aryl iodonio diazomethyl derivative with the reducing agent generates in situ an aryl iodine compound and a diazomethyl radical, actually corresponding to a carbyne equivalent (i.e. a carbon atom with three unpaired electrons). The carbyne equivalent therefore attacks an aromatic ring comprised in the substrate to form an adduct which subsequently transfers an electron to the oxidized form of the reducing agent and further loses a proton to yield the aromatic substrate functionalized with the diazomethyl radical. The inventors have shown that the method can be carried out in mild conditions and in one sole synthetic step even when the aromatic substrate of the reaction comprises functional groups or heteroatoms, which makes this process suitable for application in a late-stage functionalization approach.

Taking this into account, the inventors have found that the process of the invention is particularly efficient when the diazomethyl radical is further substituted with an electron withdrawing group, which favours the formation of the carbyne equivalent. Also, the inventors have found that the process of the invention is particularly efficient when the reducing agent is a ruthenium (II) based photosensitizer, used under light irradiation. It is advantageous as it allows having the reducing agent in a resting state in the reaction medium and being able to trigger the reaction upon light irradiation.

Apart from the alpha-aryl iodonio diazomethyl derivatives described in the state of the art, the inventors have found new compounds which can be used in the method of the invention as reagents. It is advantageous since, in comparison with the compounds described in the state of the art, these compounds are more stable upon storage, and/or are more reactive, and/or allow introducing different diazomethyl radicals.

Thus, an aspect of the invention relates to a compound of formula (I)

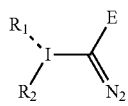

(I)

wherein:
the dotted line means that $R_1$ is attached to the iodine atom through a bond selected from a covalent bond and a ionic bond, E is a radical selected from the group consisting of the radical of formula -$G_1$, and the radical of formula -$G_2$-$G_3$ wherein:
$G_1$ and $G_3$ are independently selected from the group consisting of $(C_1$-$C_6)$haloalkyl, $(C_1$-$C_6)$alkyloxycarbonyl, benzyloxycarbonyl, a formyl group (—CHO), $(C_1$-$C_6)$alkylcarbonyl, carboxyl (—COOH), a radical of formula —$CONR_aR_b$ wherein $R_a$ and $R_b$ are each independently selected from the group consisting of hydrogen and $(C_1$-$C_6)$alkyl, halogen, nitro, $(C_1$-$C_6)$alkyloxysulfonyl, a radical of formula —P(O)(O($C_1$-$C_6$)alkyl)$_2$, nitrile and an aromatic ring system comprising from 1 to 2 6-membered aromatic rings, the members being selected from the group consisting of C, CH and N, being at least one member N, and the rings being further optionally substituted at any available position with one or more groups selected from halogen, $(C_1$-$C_6)$alkyl, $(C_1$-$C_6)$haloalkyl, $(C_1$-$C_6)$alkyloxy, $(C_1$-$C_6)$alkylcarbonyl, $(C_1$-$C_6)$alkylcarbonyloxy, $(C_1$-$C_6)$alkyloxycarbonyl, nitrile, a formyl group and nitro; and $G_2$ is a diradical selected from the group consisting of vinyl (—CH═CH—), carbonyl and an aromatic ring system comprising from 1 to 2 5- to 6-membered aromatic rings, the members being selected from the group consisting of C, CH, O, S and N, and where both the vinyl and the aromatic ring system are further optionally substituted at any available position with one or more groups selected from halogen, $(C_1$-$C_6)$alkyl, $(C_1$-$C_6)$haloalkyl, $(C_1$-$C_6)$alkyloxy, $(C_1$-$C_6)$alkylcarbonyl, $(C_1$-$C_6)$alkylcarbonyloxy, $(C_1$-$C_6)$alkyloxycarbonyl, nitrile, a formyl group and nitro;

$R_1$ is selected from the group consisting of halo, $(C_1$-$C_6)$haloalkylsulfonyloxy, $(C_1$-$C_6)$alkylsulfonyloxy, phenylsulfonyloxy, tolylsulfonyloxy, $(C_1$-$C_6)$alkylcarbonyloxy, hexafluorophosphate, tetrafluoroborate, hexafluoroantimonate, and $(C_1$-$C_6)$haloalkylcarbonyloxy;

$R_2$ is a $(C_6$-$C_{20})$aryl, optionally substituted at any available position with one or more radicals selected from the group consisting of $(C_1$-$C_6)$alkyl, $(C_1$-$C_6)$alkyloxy, $(C_1$-$C_6)$haloalkyl, $(C_1$-$C_6)$alkylcarbonyl, $(C_1$-$C_6)$alkyloxycarbonyl, and a radical of formula —X—$CH_2$-E' wherein X is a diradical selected from the group consisting of the diradicals of formula —COO—, —C(($C_1$-$C_6$)alkyl)$_2$O—, —$SO_2$—O—, —NR—O—, —B(OR)—O—, —S—O—, and —P(O)(OR)—O—, wherein R is H or $(C_1$-$C_6)$alkyl; and E' has the same meaning as E;

or, alternatively, $R_1$ and $R_2$, together with the iodine atom to which they are attached form a ring in such a way that the compound of formula (I) is a compound of formula (II)

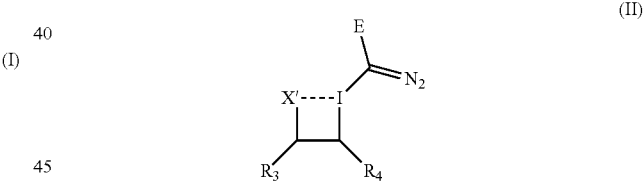

(II)

wherein:
the dotted line means that X' is attached to the iodine atom through a bond selected from a covalent bond and a ionic bond;

X' is a diradical selected from the group consisting of the diradicals of formula —COO—, —C(($C_1$-$C_6$)alkyl)$_2$O—, —$SO_2$—O—, —NR—O—, —B(OR)—O—, —S—O—, and —P(O)(OR)—O—, wherein R is H or $(C_1$-$C_6)$alkyl; and $R_3$ and $R_4$, together with the carbon atoms to which they are attached, form an aromatic ring system comprising from 1 to 2 rings, each ring comprising from 5 to 6 members, said members being selected from the group consisting of C, CH, N, NR, being R hydrogen or $(C_1$-$C_6)$alkyl, O and S; and the rings being further optionally substituted with one or more radicals selected from the group consisting of $(C_1$-$C_6)$alkyl, $(C_1$-$C_6)$alkyloxy, $(C_1$-$C_6)$haloalkyl, $(C_1$-$C_6)$alkylcarbonyl, and $(C_1$-$C_6)$alkyloxycarbonyl; and provided that the compound of formula (I) is other than a compound of formula (Ia), or (Ib), or (Ic)

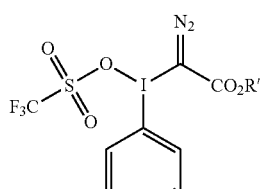
(Ia)

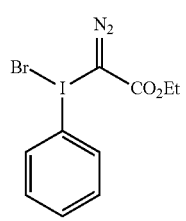
(Ib)

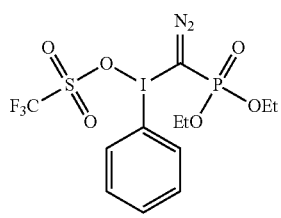
(Ic)

wherein in the compound of formula (Ia) R' is ethyl or tert-butyl.

In a second aspect, the invention relates to the use of the compound of formula (I) as defined above, or a compound of formula (Ia), (Ib) or (Ic)

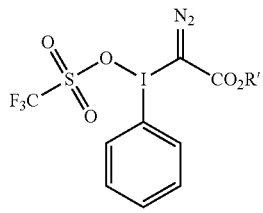
(Ia)

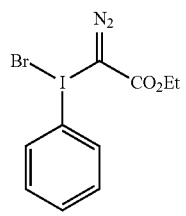
(Ib)

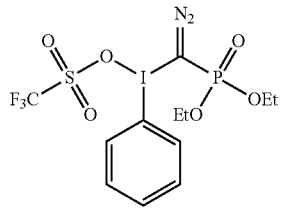
(Ic)

wherein in the compound of formula (Ia) R' is ethyl or tert-butyl as a reagent for the transfer of a group of formula —C(=N$_2$)(E) to a substrate comprising at least one aromatic or heteroaromatic ring system, being E as defined in the first aspect of the invention.

In a third aspect, the invention relates to a process of preparing a compound comprising a moiety of formula (III)

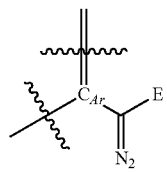
(III)

comprising the step of contacting a compound comprising the moiety of formula (IV)

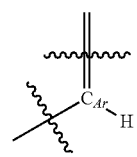
(IV)

with a compound of formula (I) as defined above or a compound selected from the compounds of formula (Ia), (Ib) and (Ic)

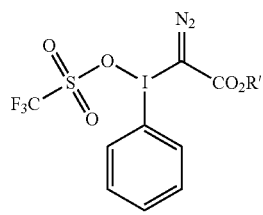
(Ia)

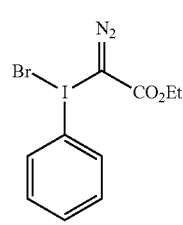
(Ib)

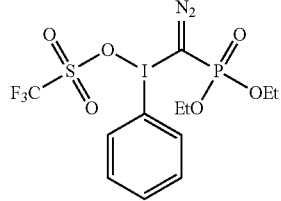
(Ic)

wherein in the compound of formula (Ia) R' is ethyl or tert-butyl; in the presence of a suitable reducing agent and in the presence of a base, wherein, in the compounds comprising the moieties of formula (III) and (IV) $C_{Ar}$ represents a carbon atom comprised in an aromatic or heteroaromatic ring system and wherein the process transforms the moiety of formula (IV) into the moiety of formula (III).

DETAILED DESCRIPTION OF THE INVENTION

All terms as used herein in this application, unless otherwise stated, shall be understood in their ordinary meaning as known in the art. Other more specific definitions for certain terms as used in the present application are as set forth below and are intended to apply uniformly through-out the specification and claims unless an otherwise expressly set out definition provides a broader definition.

For the purposes of the invention, any ranges given include both the lower and the upper end-points of the range. Ranges given, such as temperatures, times, and the like, should be considered approximate, unless specifically stated.

In the context of the invention, the term "halo" or "halogen" refers to an halogen radical, it thus refers to fluoro, chloro, bromo or iodo.

In the context of the invention, the term "alkyl" refers to a saturated linear or branched hydrocarbon group having the number of carbon atoms indicated in the description or in the claims. Examples of alkyl groups include, but are not limited to: methyl, ethyl, propyl, iso-propyl, butyl, iso-butyl, tert-butyl, pentyl, and hexyl.

In the context of the invention, the term "haloalkyl" refers to a saturated linear or branched hydrocarbon group having the number of carbon atoms indicated in the description or in the claims wherein one or more, preferably one to five, and more preferably one to three of the hydrogen atoms are replaced by an halo group. In particular embodiments of the invention, the term "haloakyl" refers to a saturated linear or branched hydrocarbon group having the number of carbon atoms indicated in the description or in the claims wherein all the hydrogen atoms are replaced by a fluoro group (also called "perfluoroalkyl"). Examples of haloalkyl groups include, but are not limited to: chloromethyl, trifluoromethyl, bromomethyl, and pentafluoroethyl.

In the context of the invention, the term "alkyloxy" refers to a saturated linear or branched hydrocarbon group having the number of carbon atoms indicated in the description or in the claims which is attached to the remainder of the formula through an ether group (—O—).

In the context of the invention, the term "alkylcarbonyl" refers to a saturated linear or branched hydrocarbon group having the number of carbon atoms indicated in the description or in the claims which is attached to the remainder of the formula through a carbonyl group (C=O).

In the context of the invention, the term "alkylcarbonyloxy" refers to a saturated linear or branched hydrocarbon group having the number of carbon atoms indicated in the description or in the claims which is attached to the remainder of the formula through a carboxyl group (—COO—) and wherein the alkyl chain is attached to the carbon atom of the carboxyl group. Similarly, the term "haloalkylcarbonyloxy" refers to a haloalkyl group as defined above which is attached to the remainder of the formula through a carboxyl group (—COO—) and wherein the haloalkyl chain is attached to the carbon atom of the carboxyl group.

In the context of the invention, the term "alkyloxycarbonyl" refers to a saturated linear or branched hydrocarbon group having the number of carbon atoms indicated in the description or in the claims which is attached to the remainder of the formula through a carboxyl group (—OOC—) and wherein the alkyl chain is attached to the oxygen atom of the carboxyl group and the C atom of the carboxyl group is attached to the remainder of the formula. Similarly, the term "benzyloxycarbonyl" refers to a benzyl group attached to the remainder of the formula through a carboxyl group (—OOC—) and wherein the benzyl is attached to the oxygen atom of the carboxyl group and the C atom of the carboxyl group is attached to the remainder of the formula.

In the context of the invention, the term "alkylsulfonyloxy" refers to a saturated linear or branched hydrocarbon group having the number of carbon atoms indicated in the description or in the claims which is attached to the remainder of the formula through a sulfonate group (—SO$_2$—O—) and wherein the alkyl chain is attached to the sulphur atom of the sulfonate group. Similarly, the term "phenylsulfonyloxy" refers to a phenyl group attached to the remainder of the formula through a sulfonate group (—SO$_2$—O—) and wherein the phenyl is attached to the sulphur atom of the sulfonate group. Similarly, the term "tolylsulfonyloxy" refers to a tolyl group attached to the remainder of the formula through a sulfonate group (—SO$_2$—O—) and wherein the tolyl is attached to the sulphur atom of the sulfonate group. Similarly, the term "haloalkylsulfonyloxy" refers to a haloalkyl group as defined above attached to the remainder of the formula through a sulfonate group (—SO$_2$—O—) and wherein the haloalkyl is attached to the sulphur atom of the sulfonate group.

In the context of the invention, the term "alkyloxysulfonyl" refers to a saturated linear or branched hydrocarbon group having the number of carbon atoms indicated in the description or in the claims which is attached to the remainder of the formula through a sulfonate group (—O—SO$_2$—) and wherein the alkyl chain is attached to the oxygen atom of the sulfonate group and the S atom of the sulfonyl group is attached to the remainder of the formula.

In the context of the invention, the term "electron withdrawing group" (also called EWG) refers to a group or molecular fragment able to withdraw electron density from the atom to which the group is attached, thereby polarizing the bond between the aforementioned atom and the EWG. Particularly, in the context of the invention, suitable electron withdrawing groups E or E' are independently selected from the group consisting of the radicals of formula -G$_1$, and the radicals of formula -G$_2$-G$_3$ wherein:

G$_1$ and G$_3$ are independently selected from the group consisting of (C$_1$-C$_6$)haloalkyl, (C$_1$-C$_6$)alkyloxycarbonyl, benzyloxycarbonyl, a formyl group (—CHO), (C$_1$-C$_6$)alkylcarbonyl, carboxyl (—COOH), a radical of formula —CONR$_a$R$_b$ wherein R$_a$ and R$_b$ are each independently selected from the group consisting of hydrogen and (C$_1$-C$_6$)alkyl, halogen, nitro, (C$_1$-C$_6$)alkyloxysulfonyl, a radical of formula —P(O)(O(C$_1$-C$_6$)alkyl)$_2$, nitrile and an aromatic ring system comprising from 1 to 2 6-membered aromatic rings, the members being selected from the group consisting of C, CH and N, being at least one member N, and the rings being further optionally substituted at any available position with one or more groups selected from halogen, (C$_1$-C$_6$)alkyl, (C$_1$-C$_6$)haloalkyl, (C$_1$-C$_6$)alkyloxy, (C$_1$-C$_6$)alkylcarbonyl, (C$_1$-C$_6$)alkylcarbonyloxy, (C$_1$-C$_6$)alkyloxycarbonyl, nitrile, a formyl group and nitro; and G$_2$ is a diradical selected from the group consisting of vinyl (—CH=CH—), carbonyl and an aromatic ring system comprising from 1 to 2 5- to 6-membered aromatic rings, the members being selected from the group consisting of C, CH, O, S and N, and where both the vinyl and the aromatic ring system are further optionally substituted at any available position with a group selected from halogen, (C$_1$-C$_6$)alkyl, (C$_1$-C$_6$)haloalkyl, (C$_1$-C$_6$)alkyloxy, (C$_1$-

$C_6$)alkylcarbonyl, ($C_1$-$C_6$)alkylcarbonyloxy, ($C_1$-$C_6$) alkyloxycarbonyl, nitrile, a formyl group and nitro.

In the context of the invention, the term "base" refers to a substance able to take protons from other substances.

In the context of the invention, the term "catalytically effective amount" refers to the fact that the amount of reducing agent is much smaller than the stoichiometric amounts of either starting materials. The amount is expressed as percentage calculated as the ratio of the number of moles of reducing agent in relation to the number of molecules of the compound incorporating the moiety of formula (IV).

In the context of the invention, the term "aryl" refers to an aromatic hydrocarbon ring system comprising the number of carbon atoms indicated in the description and claims and comprising 5 to 6-membered rings. Examples of aryl groups include, but are not limited to: phenyl, naphthyl, indenyl, anthracenyl and phenanthrenyl.

In the context of the invention, the term "suitable reducing agent" refers to a compound or system able to reduce the compound of formula (I) to a radical of formula $N_2$=C.-E (i.e. carbyne equivalent) in the conditions of the method of the invention. Alternatively, the term "suitable reducing agent" may refer to a "suitable electron source". Furthermore, the suitable reducing agent can be such that, in its oxidized form, it allows the oxidation of the reaction intermediate resulting from the attack of the radical of formula $N_2$=C.-E to the aromatic ring of the reaction substrate, in which case the reducing agent can be used in a catalytically effective amount, being regenerated in situ. Examples of suitable reducing agents include but are not limited to electrochemical cells, electrodes, photoelectrochemical means, photocatalysts, photosensitizers, or photoredox catalysts such as tris-(2,2'-bipyrimidine)ruthenium$^{2+}$, tris-(2,2'-bipyrazine)ruthenium$^{2+}$, tris-(2,2'-bipyridine)ruthenium$^{2+}$, tris-(1,10-phenanthroline)ruthenium$^{2+}$, bis-(2-(2',4'-difluorophenyl)-5-trifluoromethylpyridine)(di-tert-butylbipyridine)iridium$^+$, bis-(2-phenylpyridine)(di-tert-butylbipyridine)iridium$^+$, fac-(tris-(2,2'-phenylpyridine))iridium, particularly those based on ruthenium (II) complexes (tris-(2,2'-bipyrimidine)ruthenium$^{2+}$, tris-(2,2'-bipyrazine)ruthenium$^{2+}$, tris-(2,2'-bipyridine)ruthenium$^{2+}$, tris-(1,10-phenanthroline)ruthenium$^{2+}$).

In the context of the invention, when in the compound of formula (I) the bond between $R_1$ and the iodine atom is an ionic bond, then the compound of formula (I) may alternatively have the formula (I')

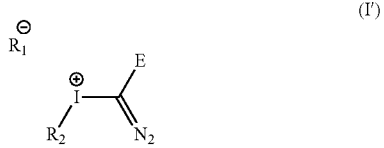

(I')

As it is mentioned above, the first aspect of the invention relates to a compound of formula (I) as defined above.

In an embodiment of the first aspect of the invention, optionally in combination with one or more features of the various embodiments described below, in the compound of formula (I), each of E and E' is independently selected from a group of formula -$G_1$ and a group of formula -$G_2$-$G_3$, wherein:

$G_1$ and $G_3$ are independently selected from the group consisting of ($C_1$-$C_6$)haloalkyl, ($C_1$-$C_6$)alkyloxycarbonyl, benzyloxycarbonyl, a formyl group (—CHO), ($C_1$-$C_6$)alkylcarbonyl, a radical of formula —CONR$_a$R$_b$ wherein R$_a$ and R$_b$ are each independently selected from the group consisting of hydrogen and ($C_1$-$C_6$) alkyl, ($C_1$-$C_6$)alkyloxysulfonyl, a radical of formula —P(O)(O($C_1$-$C_6$)alkyl)$_2$, nitrile, and phenyl; and $G_2$ is a diradical selected from the group consisting of vinyl (—CH=CH—), carbonyl and phenyl.

In another embodiment of the first aspect of the invention, optionally in combination with one or more features of the various embodiments described above or below, in the compound of formula (I), each of E and E' is independently a group of formula -$G_2$-$G_3$ wherein $G_3$ is selected from the group consisting of ($C_1$-$C_6$)haloalkyl, ($C_1$-$C_6$)alkyloxycarbonyl, benzyloxycarbonyl, a formyl group (—CHO), ($C_1$-$C_6$)alkylcarbonyl, a radical of formula —CONR$_a$R$_b$ wherein R$_a$ and R$_b$ are each independently selected from the group consisting of hydrogen and ($C_1$-$C_6$)alkyl, ($C_1$-$C_6$)alkyloxysulfonyl, a radical of formula —P(O)(O($C_1$-$C_6$)alkyl)$_2$, phenyl and nitrile; and $G_2$ is selected from vinyl and carbonyl.

In another embodiment of the first aspect of the invention, optionally in combination with one or more features of the various embodiments described above or below, in the compound of formula (I), each of E and E' is independently a group of formula -$G_2$-$G_3$ wherein $G_3$ is selected from the group consisting of ($C_1$-$C_6$)haloalkyl, ($C_1$-$C_6$)alkyloxycarbonyl, benzyloxycarbonyl, a formyl group (—CHO), ($C_1$-$C_6$)alkylcarbonyl, a radical of formula —CONR$_a$R$_b$ wherein R$_a$ and R$_b$ are each independently selected from the group consisting of hydrogen and ($C_1$-$C_6$)alkyl, ($C_1$-$C_6$)alkyloxysulfonyl, a radical of formula —P(O)(O($C_1$-$C_6$)alkyl)$_2$, phenyl and nitrile; and $G_2$ is a carbonyl group.

In another embodiment of the first aspect of the invention, optionally in combination with one or more features of the various embodiments described above or below, in the compound of formula (I), each of E and E' is independently a group of formula -$G_2$-$G_3$ wherein $G_3$ is selected from the group consisting of ($C_1$-$C_6$)haloalkyl, and phenyl and $G_2$ is a carbonyl group.

In another embodiment of the first aspect of the invention, optionally in combination with one or more features of the various embodiments described above or below, in the compound of formula (I), each of E and E' is independently a group of formula -$G_2$-$G_3$ wherein $G_3$ is phenyl and $G_2$ is a carbonyl group.

In another embodiment of the first aspect of the invention, optionally in combination with one or more features of the various embodiments described above or below, in the compound of formula (I), each of E and E' is independently a group of formula -$G_1$ selected from the group consisting of ($C_1$-$C_6$)haloalkyl, ($C_1$-$C_6$)alkyloxycarbonyl, benzyloxycarbonyl, a formyl group (—CHO), ($C_1$-$C_6$)alkylcarbonyl, a radical of formula —CONR$_a$R$_b$ wherein R$_a$ and R$_b$ are each independently selected from the group consisting of hydrogen and ($C_1$-$C_6$)alkyl, ($C_1$-$C_6$)alkyloxysulfonyl, a radical of formula —P(O)(O($C_1$-$C_6$)alkyl)$_2$, and nitrile.

In another embodiment of the first aspect of the invention, optionally in combination with one or more features of the various embodiments described above or below, in the compound of formula (I), each of E and E' is independently a group of formula -$G_1$ selected from the group consisting of ($C_1$-$C_6$)haloalkyl, ($C_1$-$C_6$)alkyloxycarbonyl, benzyloxycarbonyl, a radical of formula —CONR$_a$R$_b$ wherein R$_a$ and R$_b$ are each independently selected from the group consisting of hydrogen and ($C_1$-$C_6$)alkyl, ($C_1$-$C_6$)alkyloxysulfonyl and nitrile.

In another embodiment of the first aspect of the invention, in the compound of formula (I), each of E and E' is independently a group of formula -G$_1$ selected from the group consisting of (C$_1$-C$_6$)haloalkyl, (C$_1$-C$_6$)alkyloxycarbonyl, benzyloxycarbonyl, a radical of formula —CONR$_a$R$_b$ wherein R$_a$ and R$_b$ are each independently selected from the group consisting of hydrogen and (C$_1$-C$_6$)alkyl, (C$_1$-C$_6$)alkyloxysulfonyl and nitrile;

or; alternatively, each of E and E' is independently a group of formula -G$_2$-G$_3$, wherein:

G$_3$ is selected from the group consisting of (C$_1$-C$_6$) haloalkyl, (C$_1$-C$_6$)alkyloxycarbonyl, benzyloxycarbonyl, a formyl group (—CHO), (C$_1$-C$_6$)alkylcarbonyl, a radical of formula —CONR$_a$R$_b$ wherein R$_a$ and R$_b$ are each independently selected from the group consisting of hydrogen and (C$_1$-C$_6$)alkyl, (C$_1$-C$_6$)alkyloxysulfonyl, a radical of formula —P(O)(O(C$_1$-C$_6$)alkyl)$_2$, phenyl and nitrile; and G$_2$ is a carbonyl group.

In another embodiment of the first aspect of the invention, optionally in combination with one or more features of the various embodiments described above or below, in the compound of formula (I), each of E and E' is independently selected from the group consisting of trifluoromethyl, ethyloxycarbonyl, tert-butyloxycarbonyl, benzyloxycarbonyl, a radical of formula —CON(C$_2$H$_5$)$_2$, ethyloxysulfonyl, phenylcarbonyl and nitrile.

In another embodiment of the first aspect of the invention, optionally in combination with one or more features of the various embodiments described above or below, in the compound of formula (I), R$_1$ is selected from the group consisting of halo, (C$_1$-C$_6$)haloalkylsulfonyloxy, (C$_1$-C$_6$)alkylsulfonyloxy, phenylsulfonyloxy, tolylsulfonyloxy, (C$_1$-C$_6$)alkylcarbonyloxy, hexafluorophosphate, tetrafluoroborate, hexafluoroantimonate, and (C$_1$-C$_6$)haloalkylcarbonyloxy; and wherein the bond between R$_1$ and the iodine atom is preferably ionic.

In another embodiment of the first aspect of the invention, optionally in combination with one or more features of the various embodiments described above or below, in the compound of formula (I), R$_1$ is selected from the group consisting trifluoromethylsulfonyloxy, hexafluorophosphate and tetrafluoroborate; and wherein the bond between R$_1$ and the iodine atom is preferably ionic.

In another embodiment of the first aspect of the invention, optionally in combination with one or more features of the various embodiments described above or below, in the compound of formula (I), R$_2$ is a (C$_6$-C$_{20}$)aryl, optionally substituted at any available position with one or more radicals of formula —X—CH$_2$-E' wherein X and E' are as previously defined.

In another embodiment of the first aspect of the invention, optionally in combination with one or more features of the various embodiments described above or below, in the compound of formula (I), R$_2$ is a (C$_6$-C$_{20}$)aryl, optionally substituted at the carbon atom adjacent to the carbon atom of R$_2$ attached to the iodine atom with a radical of formula —X—CH$_2$-E' wherein X and E' are as previously defined.

In another embodiment of the first aspect of the invention, optionally in combination with one or more features of the various embodiments described above or below, in the compound of formula (I), R$_2$ is a phenyl optionally substituted at the carbon atom adjacent to the carbon atom of R$_2$ attached to the iodine atom with a radical of formula —X—CH$_2$-E' wherein X and E' are as previously defined.

In another embodiment of the first aspect of the invention, optionally in combination with one or more features of the various embodiments described above or below, in the compound of formula (I), R$_2$ is a phenyl optionally substituted at the carbon atom adjacent to the carbon atom of R$_2$ attached to the iodine atom with a radical of formula —X—CH$_2$-E' wherein X is a diradical selected from the group consisting of the diradicals of formula —COO— and —C((C$_1$-C$_6$)alkyl)$_2$O—; and E' is as previously defined.

In another embodiment of the first aspect of the invention, optionally in combination with one or more features of the various embodiments described above or below, in the compound of formula (I), R$_2$ is a phenyl optionally substituted at a carbon atom adjacent to the carbon atom of R$_2$ attached to the iodine atom with a radical of formula —X—CH$_2$-E' wherein X is a diradical of formula —COO—; and E' is as previously defined.

In another embodiment of the first aspect of the invention, optionally in combination with one or more features of the various embodiments described above or below, in the compound of formula (I), R$_2$ is a phenyl optionally substituted at a carbon atom adjacent to the carbon atom of R$_2$ attached to the iodine atom with a radical of formula —X—CH$_2$-E' wherein X is a diradical of formula —COO—; and E' is selected from the group consisting of (C$_1$-C$_6$)alkyloxycarbonyl and benzyloxycarbonyl.

In another embodiment of the first aspect of the invention, the compound of formula (I) is selected from the compounds of formula (Id), (Ie), (If), (Ig), (Ih) and (Ii):

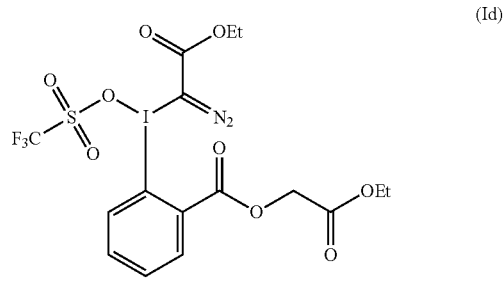

(Id)

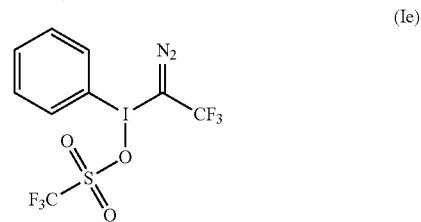

(Ie)

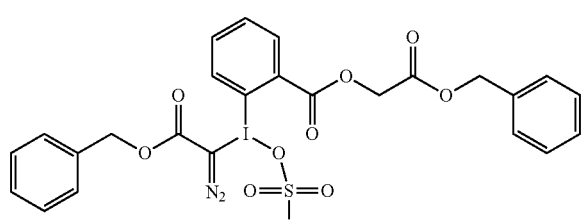

(If)

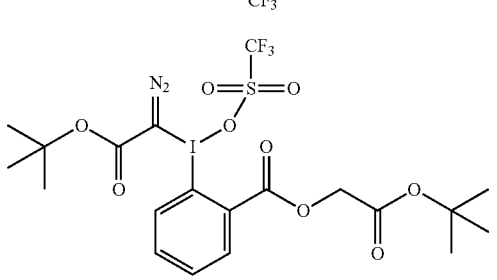

(Ig)

-continued

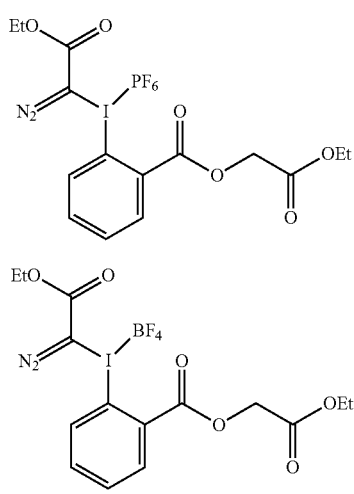

(Ih)

(Ii)

In another embodiment of the first aspect of the invention, optionally in combination with one or more features of the various embodiments described above or below, in the compound of formula (I), $R_1$ and $R_2$, together with the iodine atom to which they are attached form a ring in such a way that the compound of formula (I) is a compound of formula (II) wherein X' is a diradical selected from the group consisting of the diradicals of formula —COO—, —C(($C_1$-$C_6$)alkyl)$_2$O— and —SO$_2$—O—. Preferably, $R_1$ and $R_2$, together with the iodine atom to which they are attached form a ring in such a way that the compound of formula (I) is a compound of formula (II) wherein X' is a diradical selected from the group consisting of the diradicals of formula —COO—, and C(($C_1$-$C_6$)alkyl)$_2$O—. More preferably, $R_1$ and $R_2$, together with the iodine atom to which they are attached form a ring in such a way that the compound of formula (I) is a compound of formula (II) wherein X' is a diradical selected from the group consisting of the diradicals of formula —COO—, and C(($CH_3$)$_2$O—. In the context of the invention, when $R^2$ is a group substituted with a radical of formula —X—$CH_2$-E', the meaning of X has to be read from left to right, i.e., if for example X is —COO—, it has to be understood that the C atom of the carboxyl group is attached to the group forming $R_2$ and the O atom is attached to the —$CH_2$-E' group. In another example, when X is —NR—O—, it has to be understood that the N atom is attached to the group forming $R_2$ and the O atom is attached to the —$CH_2$-E' group. In another example, when X is —NR—O—, it has to be understood that the N atom is attached to the cycle formed by $R_3$ and $R_4$ and the O atom is attached to the —$CH_2$— group.

Similarly, in a compound of formula (II) and in a compound of formula (V) the meaning of X' and $X^2$ has also to be read from left to right. Thus, for example if X' in a compound of formula (II) is —COO—, it has to be understood that the C atom of the carboxyl group is attached to a C atom comprised in the group $R_3$ and the O atom is attached to the iodine atom. On the other hand, in a compound of formula (V) if $X^2$ is —COO—, it has to be understood that the C atom of the carboxyl group is attached to a C atom comprised in the group $R_5$ and the O atom is attached to the iodine atom.

In another embodiment of the first aspect of the invention, optionally in combination with one or more features of the various embodiments described above or below, in the compound of formula (I), $R_1$ and $R_2$, together with the iodine atom to which they are attached form a ring in such a way that the compound of formula (I) is a compound of formula (II) wherein $R_3$ and $R_4$, together with the carbon atoms to which they are attached, form an aromatic ring system comprising from 1 to 2 rings, each ring comprising from 5 to 6 members, said members being selected from the group consisting of C and CH, and the rings being further optionally substituted with one or more radicals selected from the group consisting of ($C_1$-$C_6$)alkyl, ($C_1$-$C_6$)alkyloxy, ($C_1$-$C_6$)haloalkyl, ($C_1$-$C_6$)alkylcarbonyl, and ($C_1$-$C_6$)alkyloxycarbonyl.

In another embodiment of the first aspect of the invention, optionally in combination with one or more features of the various embodiments described above or below, in the compound of formula (I), $R_1$ and $R_2$, together with the iodine atom to which they are attached form a ring in such a way that the compound of formula (I) is a compound of formula (II) wherein $R_3$ and $R_4$, together with the carbon atoms to which they are attached, form an aromatic ring system comprising from 1 to 2 rings, each ring comprising from 5 to 6 members, said members being selected from the group consisting of C and CH.

In another embodiment of the first aspect of the invention, optionally in combination with one or more features of the various embodiments described above or below, in the compound of formula (I), $R_1$ and $R_2$, together with the iodine atom to which they are attached form a ring in such a way that the compound of formula (I) is a compound of formula (II) wherein $R_3$ and $R_4$, together with the carbon atoms to which they are attached, form a phenyl ring.

In another embodiment of the first aspect of the invention, optionally in combination with one or more features of the various embodiments described above or below, in the compound of formula (I), $R_1$ is selected from the group consisting of trifluoromethylsulfonyloxy, hexafluorophosphate and tetrafluoroborate;

$R_2$ is a phenyl optionally substituted at a carbon atom adjacent to the carbon atom of $R_2$ attached to the iodine atom with a radical of formula —X—$CH_2$-E'; wherein X is a diradical selected from the group consisting of the diradicals of formula —COO—, —C(($C_1$-$C_6$)alkyl)$_2$O— and —SO$_2$—O— and E' has the same meaning as E;

or, alternatively;

$R_1$ and $R_2$, together with the iodine atom to which they are attached form a ring in such a way that the compound of formula (I) is a compound of formula (II) wherein X' is a diradical selected from the group consisting of the diradicals of formula —COO—, —C(($C_1$-$C_6$)alkyl)$_2$O— and —SO$_2$—O—; and $R_3$ and $R_4$, together with the carbon atoms to which they are attached, form a phenyl ring.

In another embodiment of the first aspect of the invention, optionally in combination with one or more features of the various embodiments described above or below, E and E' are the same.

In another embodiment of the first aspect of the invention, optionally in combination with one or more features of the various embodiments described above or below, in the compound of formula (I), $R_1$ is selected from the group consisting of trifluoromethanesulfonyloxy ($CF_3$—S(O)$_2$—O—), hexafluorophosphate and tetrafluoroborate;

$R_2$ is a phenyl optionally substituted at a carbon atom adjacent to the carbon atom of $R_2$ attached to the iodine atom with a radical of formula —X—$CH_2$-E' wherein X is a diradical of formula —COO—; and E' has the same meaning as E;

or, alternatively;

R₁ and R₂, together with the iodine atom to which they are attached form a ring in such a way that the compound of formula (I) is a compound of formula (II) wherein X' is a diradical selected from the groups consisting of the diradicals of formula —COO— and —C(CH₃)₂O—, and R₃ and R₄, together with the carbon atoms to which they are attached, form a phenyl ring.

In another embodiment of the first aspect of the invention, the compound of formula (I) is a compound of formula (II) selected from the group consisting of (IIa), (IIb), (IIc), (IId), (IIe), (IIf) and (IIg):

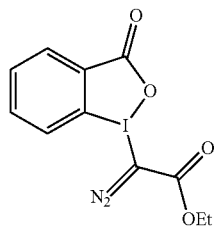
(IIa)

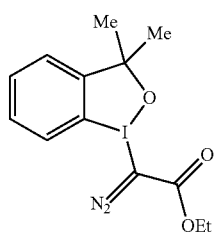
(IIb)

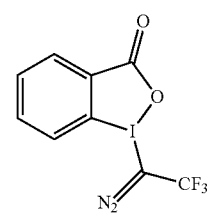
(IIc)

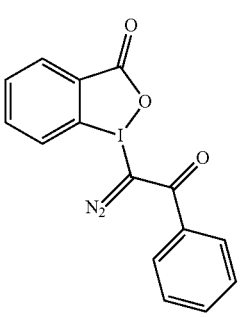
(IId)

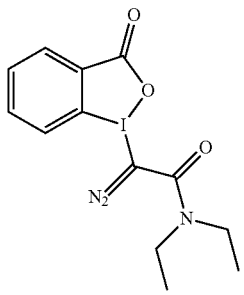
(IIe)

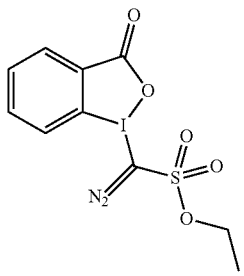
(IIf)

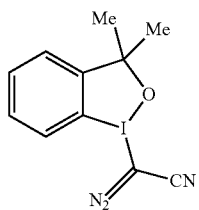
(IIg)

The compounds of the invention are useful reagents for the transfer of a group of formula —C(=N₂)-E onto a substrate bearing an aromatic or heteroaromatic moiety. As it mentioned above, the second aspect of the invention relates to the use of the compound of formula (I) as defined in the first aspect of the invention, or a compound of formula (Ia), (Ib) or (Ic)

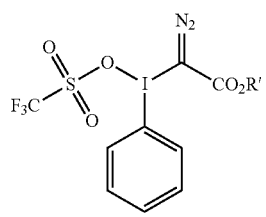
(Ia)

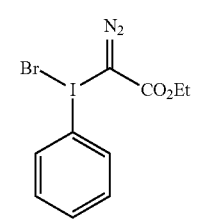
(Ib)

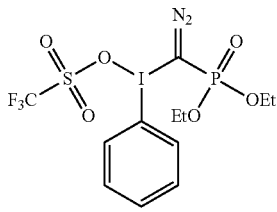
(Ic)

wherein in the compound of formula (Ia) R' is ethyl or tert-butyl; as a reagent for the transfer of a group of formula —C(=N$_2$)(E) to a substrate comprising at least one aromatic or heteroaromatic ring system, being E as defined above.

It is advantageous as the transfer of this group can be carried out in one step, under mild conditions and in the presence of a broad range of functional groups onto the reaction substrate.

A third aspect of the invention relates to a process of preparing a compound comprising a moiety of formula (III) as defined above, comprising the step of contacting a compound comprising the moiety of formula (IV) with a compound of formula (I) or a compound selected from the formula (Ia), (Ib) and (Ic) as defined above.

In an embodiment of the third aspect of the invention, the compound comprising a moiety of formula (IV) comprises at least one C—H aromatic bond, wherein said carbon atom is a member of an aromatic or heteroaromatic ring system comprised in the molecule.

In another embodiment of the third aspect of the invention, optionally in combination with one or more features of the various embodiments described above or below, the compound comprising a moiety of formula (IV) comprises at least a ring system comprising from one to two 5 to 6 membered rings, being at least one of said rings aromatic, the members of the rings being selected from the group consisting of C, CH, CH$_2$, N, NH, O, S, and P, and the aromatic ring being further optionally substituted. In a preferred embodiment of the third aspect of the invention, optionally in combination with one or more features of the various embodiments described above or below, the compound comprising a moiety of formula (IV) comprises at least a ring system comprising from one to two 5 to 6 membered rings, being at least one of said rings aromatic, the members of the rings being selected from the group consisting of C, CH, CH$_2$, N, NH, O, S, and P, and the aromatic ring being further optionally substituted with one or more radicals of formula Q selected from the group consisting of (C$_1$-C$_6$)alkyl, (C$_1$-C$_6$)alkyloxy, (C$_1$-C$_6$)haloalkyl, (C$_1$-C$_6$)alkylcarbonyl, (C$_1$-C$_6$)alkyloxycarbonyl, (C$_1$-C$_6$)alkylcarbonyloxy, formyl (—CHO), cyano, nitro, (C$_1$-C$_6$)alkylaminocarbonyl, (C$_1$-C$_6$)alkylcarbonylamino, (C$_1$-C$_6$)alkyloxycarbonylamino (such as a tert-butyloxycarbonylamino, or Boc group), halo, and [(C$_1$-C$_6$)alkyl]$_2$boronate, wherein in said Q radicals the (C$_1$-C$_6$)alkyl is further optionally substituted with one or more radicals of formula Q.

In another embodiment of the third aspect of the invention, optionally in combination with one or more features of the various embodiments described above or below, the compound comprising a moiety of formula (IV) comprises at least a ring system comprising from one to two 5 to 6 membered rings, being at least one of said rings aromatic, the members of the rings being selected from the group consisting of C, CH, CH$_2$, N, and O, and the aromatic ring being further optionally substituted with one or more radicals of formula Q selected from the group consisting of (C$_1$-C$_6$)alkyl, (C$_1$-C$_6$)alkyloxy, (C$_1$-C$_6$)haloalkyl, (C$_1$-C$_6$)alkylcarbonyl, (C$_1$-C$_6$)alkyloxycarbonyl, (C$_1$-C$_6$)alkylcarbonyloxy, formyl (—CHO), cyano, nitro, (C$_1$-C$_6$)alkylaminocarbonyl, (C$_1$-C$_6$)alkylcarbonylamino, (C$_1$-C$_6$)alkyloxycarbonylamino (such as a tert-butyloxycarbonylamino, or Boc group), halo, and [(C$_1$-C$_6$)alkyl]$_2$boronate.

In another embodiment of the third aspect of the invention, optionally in combination with one or more features of the various embodiments described above or below, the compound comprising a moiety of formula (IV) is selected from the group consisting of a drug, a drug intermediate, a polymer, a biomolecule (proteins, enzymes, peptides, antibodies, nucleic acid sequences), an aminoacid derivative, a biologically active ingredient, a polyaromatic compound, a carbon nanotube, graphene, graphene oxide, fullerene and a small organic molecule.

In another embodiment of the third aspect of the invention, optionally in combination with one or more features of the various embodiments described above or below, the compound comprising a moiety of formula (IV) is selected from the group consisting of benzene, toluene, xylene, anisol, N-Boc aniline, iodobenzene, phenyl acetate, methyl benzoate, 1-(tert-butyl)-4-methylbenzene, 1-(fluoro)-4-methylbenzene, 1-(trifluoromethyl)-4-methylbenzene, methyl 4-methylbenzoate, 1-(p-tolyl)ethanone, 4,4,5,5-tetramethyl-2-(p-tolyl)-1,3,2-dioxaborolane, naphthalene, 1-(4-methoxyphenyl)ethanone, mesitylene, methyl 2-((tert-butoxycarbonyl)amino)-3-phenylpropanoate, 3-hydroxy-13-methyl-7,8,9,11,12,13,15,16-octahydro-6H-cyclopenta[a]phenanthren-17(14H)-one, N-Boc duloxetine, N-Boc paroxetine, 2,6-di-tert-butyl pyridine, and 4-methyl-2,6-di-tert-butyl-pyridine.

As illustrated in the Examples below, the process of the invention can be carried out on a wide range of reaction substrates bearing various functional groups. It is advantageous as this allows for the introduction of the diazomethyl group at a late-stage of the synthetic procedure, which can be useful for the diazomethylation of highly functionalized compounds such as biomolecules (peptides, nucleic acids, antibodies, enzymes, etc), pharmaceutical drugs and drug intermediates. The diazomethyl group is a carbene precursor and is therefore prompt to versatile reactivity, thereby allowing for instance to further modify the diazomethylated product and introduce new properties.

In another embodiment of the third aspect of the invention, optionally in combination with one or more features of the various embodiments described above or below, the process is carried out in the presence of a compound of formula (I) as defined in any of the embodiments described above for the first aspect of the invention, or a compound of formula (Ia), (Ib) or (Ic) as defined above.

In a preferred embodiment of the third aspect of the invention, optionally in combination with one or more features of the various embodiments described above or below, the process is carried out in the presence of a compound of formula (I) selected from the group consisting of the compounds of formulae (Id), (Ie), (Ih), (Ii), (IIa) and (IIb).

In another embodiment of the third aspect of the invention, optionally in combination with one or more features of the various embodiments described above or below, the process is carried out in the presence of a suitable reducing agent selected from the group consisting of an electrode, a metal salt, a photoelectrochemical mean, a photocatalyst, a photosensitizer and a photoredox catalyst.

In a preferred embodiment, optionally in combination with one or more features of the various embodiments described above or below, the third aspect of the invention relates to a process wherein the suitable reducing agent is a photoredox catalyst that is used in a catalytically effective amount.

In a preferred embodiment of the third aspect of the invention, optionally in combination with one or more features of the various embodiments described above or below, the process is carried out in the presence of catalytically effective amount of a photoredox catalyst as suitable reducing agent wherein the photoredox catalyst is selected from the group consisting of the salts of tris-(2,2'-bipyrimidine)ruthenium$^{2+}$, tris-(2,2'-bipyrazine)ruthenium$^{2+}$, tris-(2,2'-bipyridine)ruthenium$^{2+}$, tris-(1,10-phenanthroline)ruthenium$^{2+}$, bis-(2-(2',4'-difluorophenyl)-5-trifluoromethylpyridine)(di-tert-butylbipyridine)iridium$^{+}$, bis-(2-phenylpyridine)(di-tert-butylbipyridine)iridium$^{+}$, fac-(tris-(2,2'-phenylpyridine))iridium.

In a more preferred embodiment of the third aspect of the invention, optionally in combination with one or more features of the various embodiments described above or below, the process is carried out in the presence of a catalytically effective amount of a photoredox catalyst as suitable reducing agent wherein the photoredox catalyst is selected from the group consisting of the salts of tris-(2,2'-bipyrimidine)ruthenium$^{2+}$, tris-(2,2'-bipyrazine)ruthenium$^{2+}$, tris-(2,2'-bipyridine)ruthenium$^{2+}$, and tris-(1,10-phenanthroline)ruthenium$^{2+}$.

In an even more preferred embodiment of the third aspect of the invention, optionally in combination with one or more features of the various embodiments described above or below, the process is carried out in the presence of a catalytically effective amount of a photoredox catalyst as suitable reducing agent wherein the photoredox catalyst is tris-(2,2'-bipyridine)ruthenium$^{2+}$ hexafluorophosphate.

In another embodiment of the third aspect of the invention, optionally in combination with one or more features of the various embodiments described above or below, when the suitable reducing agent is selected from the group consisting of a photoelectrochemical mean, a photocatalyst, a photosensitizer and a photoredox catalyst, then the process is preferably carried out under light irradiation. In a more particular embodiment, optionally in combination with one or more features of the various embodiments described above or below, the suitable reducing agent is a photoredox catalyst that is used in a catalytically effective amount, and the process is carried out under light irradiation.

In a particular embodiment of the third aspect of the invention, optionally in combination with one or more features of the various embodiments described above or below, the suitable reducing agent is a salt of formula A-Y wherein A is a cation selected from the group consisting of tris-(2,2'-bipyrimidine)ruthenium$^{2+}$, tris-(2,2'-bipyrazine)ruthenium$^{2+}$, tris-(2,2'-bipyridine)ruthenium$^{2+}$, tris-(1,10-phenanthroline)ruthenium$^{2+}$, bis-(2-(2',4'-difluorophenyl)-5-trifluoromethylpyridine)(di-tert-butylbipyridine)iridium$^{+}$, bis-(2-phenylpyridine)(di-tert-butylbipyridine)iridium$^{+}$, and fac-(tris-(2,2'-phenylpyridine))iridium$^{+}$;

and Y is an anion selected from the group consisting of tetrafluoroborate, hexafluorophosphate, chloride, and tetra(pentafluorophenyl)borate.

In a particular embodiment of the third aspect of the invention, optionally in combination with one or more features of the various embodiments described above or below, the suitable reducing agent is a tris-(2,2'-bipyridine)ruthenium$^{2+}$ bis hexafluorophosphate that is used in a catalytically effective amount, and the irradiation light is visible light.

In another embodiment of the third aspect of the invention, optionally in combination with one or more features of the various embodiments described above or below, the process is carried out in the presence of a base selected from the group consisting of alkaline carbonate salts, alkaline earth carbonate salts, alkaline bicarbonate salts, alkaline earth bicarbonate salts, alkaline $(C_1-C_6)$alkyloxide salts, a compound of formula $N[(C_1-C_6)alkyl]_3$, N-methyl morpholine, and pyridine optionally substituted with one or more $(C_1-C_6)$alkyl groups.

In a preferred embodiment of the third aspect of the invention, optionally in combination with one or more features of the various embodiments described above or below, the process is carried out in the presence of a base selected from the group consisting of alkaline bicarbonate salts, alkaline earth bicarbonate salts, and pyridine optionally substituted with one or more $(C_1-C_6)$alkyl groups.

In a more preferred embodiment of the third aspect of the invention, optionally in combination with one or more features of the various embodiments described above or below, the process is carried out in the presence of a base selected from the group consisting of sodium hydrogen carbonate and 2,6-di-tert-butylpyridine. More preferably, the base is sodium hydrogen carbonate.

In another embodiment of the third aspect of the invention, optionally in combination with one or more features of the various embodiments described above or below, the process is carried out in the presence of a polar aprotic solvent.

In a preferred embodiment of the third aspect of the invention, optionally in combination with one or more features of the various embodiments described above or below, the polar aprotic solvent is selected from the group consisting of acetonitrile, acetone and dichloromethane. More preferably, optionally in combination with one or more features of the various embodiments described above or below, the polar aprotic solvent is acetonitrile.

In another embodiment of the third aspect of the invention, optionally in combination with one or more features of the various embodiments described above or below, the process is carried out at room temperature.

In another embodiment of the third aspect of the invention, optionally in combination with one or more features of the various embodiments described above or below, the process is carried out with a power of light irradiation comprised between 3 and 4 W.

In another embodiment of the third aspect of the invention, optionally in combination with one or more features of the various embodiments described above or below, the molar ratio of the compound comprising the moiety of formula (IV) to the compound of formula (I), (Ia), (Ib) or (Ic) is comprised from 3:1 to 1:2. Preferably, the molar ratio of the compound comprising the moiety of formula (IV) to the compound of formula (I), (Ia), (Ib) or (Ic) is comprised from 2:1 to 1:1.5.

In another embodiment of the third aspect of the invention, optionally in combination with one or more features of the various embodiments described above or below, the molar ratio of the compound comprising the moiety of formula (IV) to the base is comprised from 1:3 to 2:3.

In another embodiment of the third aspect of the invention, optionally in combination with one or more features of the various embodiments described above or below, when the suitable reducing agent is a photoredox catalyst used in a catalytically effective amount, the molar ratio of the compound comprising the moiety of formula (IV) to the reducing agent is comprised from 1000:1 to 100:1.

In another embodiment, optionally in combination with one or more features of the various embodiments described above or below, the process of the third aspect further comprises the previous step of preparing a compound of formula (I), which comprises contacting a compound of formula (V)

wherein $X^2$ is a diradical selected from the group consisting of the diradicals of formula —COO—, —C(($C_1$-$C_6$)alkyl)$_2$O—, —SO$_2$—O—, —NR—O—, —B(OR)—O, —S—O—, and —P(O)(OR)—O—, wherein R is H or ($C_1$-$C_6$)alkyl, with a compound of formula (($C_1$-$C_6$)alkyl)$_3$Si—$R_1$ (VI) and a compound of formula $N_2$=CH-E (VII) in the presence of a polar aprotic solvent; and optionally in the presence of a base wherein:

$R_5$ is a ($C_1$-$C_6$)alkyl, $R_2$' is a ($C_6$-$C_{20}$)aryl, optionally substituted at any available position with one or more radicals selected from the group consisting of ($C_1$-$C_6$)alkyl, ($C_1$-$C_6$)alkyloxy, ($C_1$-$C_6$)haloalkyl, ($C_1$-$C_6$)alkylcarbonyl, and ($C_1$-$C_6$)alkyloxycarbonyl, or, alternatively, $R_5$ and $R_2$', together with the atoms to which they are attached, form an aromatic ring system comprising from 1 to 2 rings, each ring comprising from 5 to 6 members, said members being selected from the group consisting of C, CH, N, NR, being R hydrogen or ($C_1$-$C_6$)alkyl, O and S; and the rings being further optionally substituted with one or more radicals selected from the group consisting of ($C_1$-$C_6$)alkyl, ($C_1$-$C_6$)alkyloxy, ($C_1$-$C_6$)haloalkyl, ($C_1$-$C_6$)alkylcarbonyl, and ($C_1$-$C_6$)alkyloxycarbonyl; and $R_7$ is a ($C_1$-$C_6$)alkyloxycarbonyl or a ($C_1$-$C_6$)alkyloxy.

It also forms part of the invention a process for the preparation of a compound of formula (I), which comprises contacting a compound of formula (V)

as defined above, with a compound of formula (($C_1$-$C_6$)alkyl)$_3$Si—$R_1$(VI) and a compound of formula $N_2$=CH-E (VII) as defined above in the presence of a polar aprotic solvent; and optionally in the presence of a base.

In a particular embodiment, optionally in combination with one or more features of the various embodiments described above or below, in the compound of formula (V), $R_5$ and $R_2$', together with the atoms to which they are attached, form a ($C_6$-$C_{20}$)aryl substituted at any available position with one or more radicals selected from the group consisting of ($C_1$-$C_6$)alkyl, ($C_1$-$C_6$)alkyloxy, ($C_1$-$C_6$)haloalkyl, ($C_1$-$C_6$)alkylcarbonyl, and ($C_1$-$C_6$)alkyloxycarbonyl.

In a preferred embodiment, optionally in combination with one or more features of the various embodiments described above or below, in the compound of formula (V):

$X^2$ is a diradical of formula —COO—, $R_5$ is a ($C_1$-$C_6$)alkyl, $R_2$' is a phenyl ring, and $R_7$ is a ($C_1$-$C_6$)alkyloxycarbonyl;

or, alternatively, $X^2$ is a diradical selected from the group consisting of the diradicals of formula —COO— and —C(($C_1$-$C_6$)alkyl)$_2$O—, $R_5$ and $R_2$', together with the atoms to which they are attached, form a phenyl ring; and $R_7$ is a ($C_1$-$C_6$)alkyloxycarbonyl or a ($C_1$-$C_6$)alkyloxy.

In another embodiment, optionally in combination with one or more features of the various embodiments described above or below, the process of the third aspect further comprises the previous step of preparing a compound of formula (I), which comprises contacting a compound of formula (V)

wherein $X^2$ is a diradical selected from the group consisting of the diradicals of formula —COO—, —C(($C_1$-$C_6$)alkyl)$_2$O—, —SO$_2$—O—, —NR—O—, —B(OR)—O, —S—O—, and —P(O)(OR)—O—, wherein R is H or ($C_1$-$C_6$)alkyl, with a compound of formula (($C_1$-$C_6$)alkyl)$_3$Si—$R_1$(VI) and a compound of formula $N_2$=CH-E (VII) in the presence of a polar aprotic solvent; and optionally in the presence of a base, wherein:

$R_5$ is a ($C_1$-$C_6$)alkyl, $R_2$' is a ($C_6$-$C_{20}$)aryl, optionally substituted at any available position with one or more radicals selected from the group consisting of ($C_1$-$C_6$)alkyl, ($C_1$-$C_6$)alkyloxy, ($C_1$-$C_6$)haloalkyl, ($C_1$-$C_6$)alkylcarbonyl, and ($C_1$-$C_6$)alkyloxycarbonyl, or, alternatively, $R_5$ and $R_2$', together with the atoms to which they are attached, form an aromatic ring system comprising from 1 to 2 rings, each ring comprising from 5 to 6 members, said members being selected from the group consisting of C, CH, N, NR, being R hydrogen or ($C_1$-$C_6$)alkyl, O and S; and the rings being further optionally substituted with one or more radicals selected from the group consisting of ($C_1$-$C_6$)alkyl, ($C_1$-$C_6$)alkyloxy, ($C_1$-$C_6$)haloalkyl, ($C_1$-$C_6$)alkylcarbonyl, and ($C_1$-$C_6$)alkyloxycarbonyl; or, alternatively, $R_5$ and $R_2$', together with the atoms to which they are attached, form a ($C_6$-$C_{20}$)aryl substituted at any available position with one or more radicals selected from the group consisting of ($C_1$-$C_6$)alkyl, ($C_1$-$C_6$)alkyloxy, ($C_1$-$C_6$)haloalkyl, ($C_1$-$C_6$)alkylcarbonyl, and ($C_1$-$C_6$)alkyloxycarbonyl;

$R_7$ is a ($C_1$-$C_6$)alkyloxycarbonyl or a ($C_1$-$C_6$)alkyloxy; and wherein:

(i) when in the compound of formula (I) $R_1$ is selected from the group consisting of halo, ($C_1$-$C_6$)haloalkylsulfonyloxy, $(C_1-C_6)$alkylsulfonyloxy, phenylsulfonyloxy, tolylsulfonyloxy, $(C_1-C_6)$alkylcarbonyloxy, and $(C_1-C_6)$haloalkylcarbonyloxy; and $R_2$ is a $(C_6-C_{20})$aryl, optionally substituted at any available position with one or more radicals selected from the group consisting of $(C_1-C_6)$alkyl, $(C_1-C_6)$alkyloxy, $(C_1-C_6)$haloalkyl, $(C_1-C_6)$alkylcarbonyl, and $(C_1-C_6)$alkyloxycarbonyl; then in the compound of formula (V), $X^2$ is —COO—, $R_5$ is a $(C_1-C_6)$alkyl, $R_2'$ is a $(C_6-C_{20})$aryl, optionally substituted at any available position with one or more radicals selected from the group consisting of $(C_1-C_6)$alkyl, $(C_1-C_6)$alkyloxy, $(C_1-C_6)$haloalkyl, $(C_1-C_6)$alkylcarbonyl, and $(C_1-C_6)$alkyloxycarbonyl, and $R_7$ is a $(C_1-C_6)$alkyloxycarbonyl; and the molar ratio of the compound of formula (VII) to the compound of formula (V) is preferably comprised from 1:1 to 2:1; or, alternatively, (ii) when in the compound of formula (I) $R_1$ is selected from the group consisting of halo, $(C_1-C_6)$haloalkylsulfonyloxy, $(C_1-C_6)$alkylsulfonyloxy, phenylsulfonyloxy, tolylsulfonyloxy, $(C_1-C_6)$alkylcarbonyloxy, and $(C_1-C_6)$haloalkylcarbonyloxy; and $R_2$ is a $(C_6-C_{20})$aryl substituted at any available position with one or more radicals selected from the group consisting of $(C_1-C_6)$alkyl, $(C_1-C_6)$alkyloxy, $(C_1-C_6)$haloalkyl, $(C_1-C_6)$alkylcarbonyl, $(C_1-C_6)$alkyloxycarbonyl and the radicals of formula —X—CH$_2$-E', said compound of formula (I) comprising at least one radical of formula —X—CH$_2$-E', then in the compound of formula (V), $R_5$ and $R_2'$, together with the atoms to which they are attached, form a $(C_6-C_{20})$aryl substituted at any available position with one or more radicals selected from the group consisting of $(C_1-C_6)$alkyl, $(C_1-C_6)$alkyloxy, $(C_1-C_6)$haloalkyl, $(C_1-C_6)$alkylcarbonyl, and $(C_1-C_6)$alkyloxycarbonyl; and $R_7$ is a $(C_1-C_6)$alkyloxy; and the molar ratio of the compound of formula (VII) to the compound of formula (V) is preferably higher than 2:1 or, alternatively, (iii) when in the compound of formula (I) $R_1$ and $R_2$, together with the iodine atom to which they are attached form a ring in such a way that the compound of formula (I) is a compound of formula (II); then the process is carried out in the presence of a base, and in the compound of formula (V), $R_5$ and $R_2'$ form an aromatic ring system comprising from 1 to 2 rings, each ring comprising from 5 to 6 members, said members being selected from the group consisting of C, CH, N, NR, being R hydrogen or $(C_1-C_6)$alkyl, O and S; and the rings being further optionally substituted with one or more radicals selected from the group consisting of $(C_1-C_6)$alkyl, $(C_1-C_6)$alkyloxy, $(C_1-C_6)$haloalkyl, $(C_1-C_6)$alkylcarbonyl, and $(C_1-C_6)$alkyloxycarbonyl; and $R_7$ is a $(C_1-C_6)$alkyloxycarbonyl; or, alternatively, (iv) when in the compound of formula (I) $R_1$ is selected from hexafluorophosphate, hexafluoroantimonate and tetrafluoroborate and $R_2$ is a $(C_6-C_{20})$aryl optionally substituted at any available position with one or more radicals selected from the group consisting of $(C_1-C_6)$alkyl, $(C_1-C_6)$alkyloxy, $(C_1-C_6)$haloalkyl, $(C_1-C_6)$alkylcarbonyl, $(C_1-C_6)$alkyloxycarbonyl and the radicals of formula —X—CH$_2$-E'; then the product resulting from the processes described in the step (i) or in the step (ii) above is further contacted with an aqueous saturated solution of sodium hexafluorophosphate when $R_1$ is hexafluorophosphate, an aqueous saturated solution of sodium hexafluoroantimonate when $R_1$ is hexafluoroantimonate, or with an aqueous saturated solution of sodium tetrafluoroborate when $R_1$ is tetrafluoroborate.

Throughout the description and claims the word "comprise" and variations of the word, are not intended to exclude other technical features, additives, components, or steps. Additional objects, advantages and features of the invention will become apparent to those skilled in the art upon examination of the description or may be learned by practice of the invention. The following examples and drawings are provided by way of illustration, and they are not intended to be limiting of the present invention. Furthermore, the present invention covers all possible combinations of particular and preferred embodiments described herein.

EXAMPLES

Compound (Ia) was prepared following the procedure reported in Weiss et al, Angew. Chem., Int. Ed. 1994, 33 (19), 1952-1953.

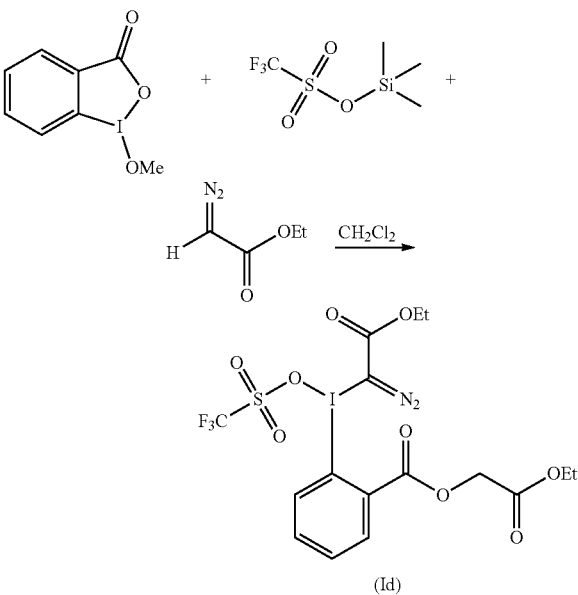

Example 1: Preparation of (1-diazo-2-ethoxy-2-oxoethyl)(2-(2-ethoxy-2-oxoethoxy)carbonylphenyl) iodonium Trifluoromethanesulfonate A solution of 1-methoxy-1,2-benziodoxol-3(1H)-one (180 mg, 0.65 mmol, 1.0 eq.) in dichloromethane (2.5 mL, 0.25 M) was treated with trimethylsilyl trifluoromethanesulfonate (0.12 mL, 0.65 mmol, 1.0 eq.) at room temperature. Then ethyl diazoacetate (0.15 mL, 1.43 mmol, 2.2 eq) was added dropwise and the reaction mixture was stirred for 1 hour at room temperature until a clear yellow solution was obtained. Solvent was removed under vacuum and the resulting solid was recrystallized from a mixture of diethyl ether/dichloromethane (5:1) during 12 hours at −30° C. The product was collected by filtration, washed with cold diethyl ether (200 mL), dried under high vacuum and stored at −30° C. as a yellow solid (572 mg, 96%).

$^1$H NMR (400 MHz, DMSO-$d_6$) δ 8.38 (dd, J=7.5, 1.9 Hz, 1H), 8.32 (dd, J=8.0, 1.2 Hz, 1H), 8.00 (td, J=7.7, 1.9 Hz, 1H), 7.95 (td, J=7.4, 1.3 Hz, 1H), 5.15 (s, 2H), 4.30-4.19 (m, 4H), 1.26-1.19 (m, 6H); $^{13}$C NMR (101 MHz, DMSO-$d_6$) δ 167.79, 167.15, 162.01, 138.10, 133.76, 133.08, 133.03, 126.70, 121.09 (q, J=324.21), 118.14, 64.09, 61.87, 14.51, 14.39. $^{19}$F NMR (376 MHz, DMSO-$d_6$): δ −77.87. Differential scanning calorimetry (DSC) analysis showed that IIa is stable up to 101.74° C.

Example 2: Preparation of 1-(1-diazo-2-ethoxy-2-oxoethyl)-1,2-benziodoxol-3(1H)-one (IIa)

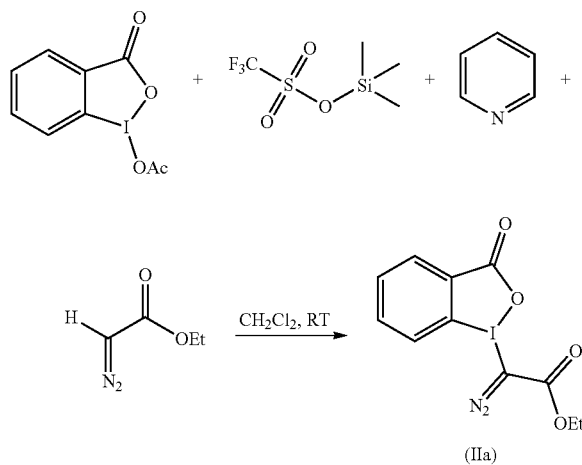

(IIa)

A solution of 1-acetoxy-1,2-benziodoxol-3(1H)-one (200 mg, 0.65 mmol, 1.0 eq.) in dichloromethane 2.5 mL (0.25 M) was treated with trimethylsilyl trifluoromethanesulfonate (0.12 mL, 0.65 mmol, 1.0 eq.) at room temperature. After 10 min of stirring, a solution of pyridine (0.053 ml, 0.65 mmol, 1.0 eq) in dichloromethane (0.5 ml) was added. The resulted suspension was additionally stirred for 2 h at room temperature. Ethyl diazoacetate (0.08 mL, 0.76 mmol, 1.2 eq) was added and the mixture was stirred until a clear yellow solution was obtained. The solution was washed with distilled water and dried with anhydrous sodium sulfate. Solvent was removed under vacuum to afford a yellowish solid. The contained pyridine salt was removed by recrystallization (3 times) from dichloromethane during 12 hours at −30° C. The resulting filtrate was evaporated under vacuum and the product was collected as a yellow solid (63 mg, 27% yield), washed with cold diethyl ether (20 mL), dried under high vacuum and stored at −30° C.

$^1$H NMR (400 MHz, DMSO-$d_6$) δ 8.10 (dd, J=7.4, 1.7 Hz, 1H), 7.89 (d, J=8.2 Hz, 1H), 7.83 (ddd, J=8.3, 7.0, 1.7 Hz, 1H), 7.76 (td, J=7.2, 1.2 Hz, 1H), 4.24 (q, J=7.1 Hz, 2H), 1.21 (t, J=7.1 Hz, 3H); $^{13}$C NMR (101 MHz, DMSO-$d_6$) δ 167.42, 164.76, 135.59, 133.35, 132.47, 131.88, 128.19, 117.67, 63.47, 15.19. Differential scanning calorimetry (DSC) analysis showed that IIa is stable up to 91.28° C.

Example 3: Preparation of 1-(1-diazo-2-ethoxy-2-oxoethyl)-1,3-dihydro-3,3-dimethyl-1,2-benziodoxole (IIb)

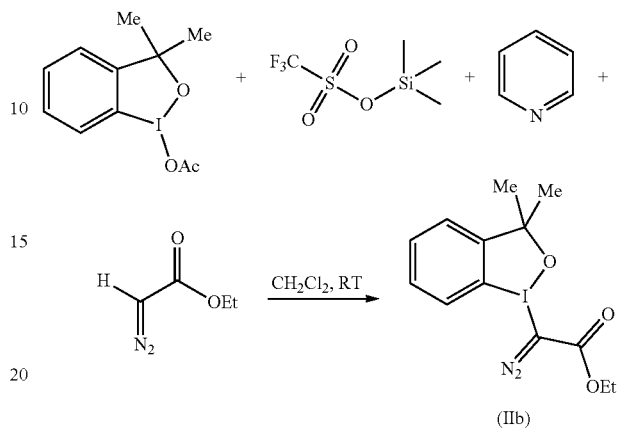

(IIb)

A solution of the 3,3-dimethyl-1-acetoxy-1,2-benziodoxole (180 mg, 0.65 mmol, 1.0 eq.) in dichloromethane 2.5 mL (0.25 M) was treated with trimethylsilyl trifluoromethanesulfonate (0.12 mL, 0.65 mmol, 1.0 eq.) at room temperature. After 10 minutes of stirring, a solution of pyridine (0.053 ml, 0.65 mmol, 1.0 eq) in dichloromethane (0.5 ml) was added. The resulted suspension was additionally stirred for 2 hours at room temperature. Ethyl diazoacetate (0.08 mL, 0.76 mmol, 1.2 eq) was added and the mixture was stirred until a clear yellow solution was obtained. The solution was cautiously washed with distilled water and dried with anhydrous sodium sulfate. Solvents were removed under vacuum and the residue was purified by flash chromatography (EA:Hexane=1:1 as eluent) to afford a yellowish oil (96 mg, 40% yield). $^1$H NMR (400 MHz, Chloroform-d) δ 7.51 (ddd, J=7.5, 6.4, 1.8 Hz, 1H), 7.45-7.38 (m, 2H), 7.37-7.31 (m, 1H), 4.22 (q, J=7.1 Hz, 2H), 1.48 (s, 6H), 1.25 (d, J=7.1 Hz, 3H); $^{13}$C NMR (126 MHz, CDCl$_3$) δ 177.30, 149.34, 130.38, 129.91, 129.87, 126.17, 115.68, 84.54, 60.86, 29.18, 21.45, 14.44.

Example 4: Preparation of (1-diazo-2,2,2-trifluoroethyl)(phenyl)iodonium Trifluoromethanesulfonate (Ie)

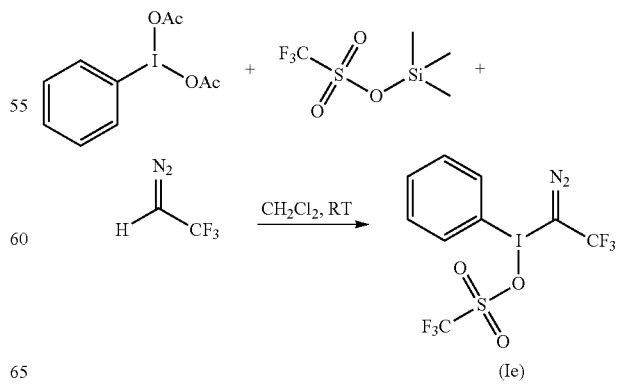

(Ie)

A solution of phenyliodoso diacetate (209 mg, 0.65 mmol, 1.0 eq.) in dichloromethane (2.5 mL, 0.25 M) was treated with trimethylsilyl trifluoromethanesulfonate (0.12 mL, 0.65 mmol, 1.0 eq.) at room temperature. Then trifluoromethyl diazomethane (0.35M, 4.0 mL, 1.43 mmol, 2.2 eq) was added dropwise and the reaction mixture was stirred for 1 hour at room temperature. Solvent was removed under vacuum and the crude was recrystallized from a mixture of diethyl ether/dichloromethane (5:1) during 12 hours at −30° C. The product was collected by filtration, washed with cold diethyl ether (200 mL), dried under high vacuum and stored at −30° C. Yellow solid (208 mg, 70%).

$^1$H NMR (400 MHz, Acetonitrile-d3) δ 8.21-8.14 (m, 2H), 7.84-7.80 (m, 1H), 7.68-7.61 (m, 2H); $^{13}$C NMR (101 MHz, Acetonitrile-d3) δ 137.42, 135.30, 133.73, 132.42, 129.11 (q, J=280.78); $^{19}$F NMR (376 MHz, CD$_3$CN) δ −55.47, −79.43. Differential scanning calorimetry (DSC) analysis showed that IIa is stable up to 93.02° C.

Example 5: Preparation of 1-(1-diazo-2,2,2-trifluoroethyl)-1,2-Benziodoxol-

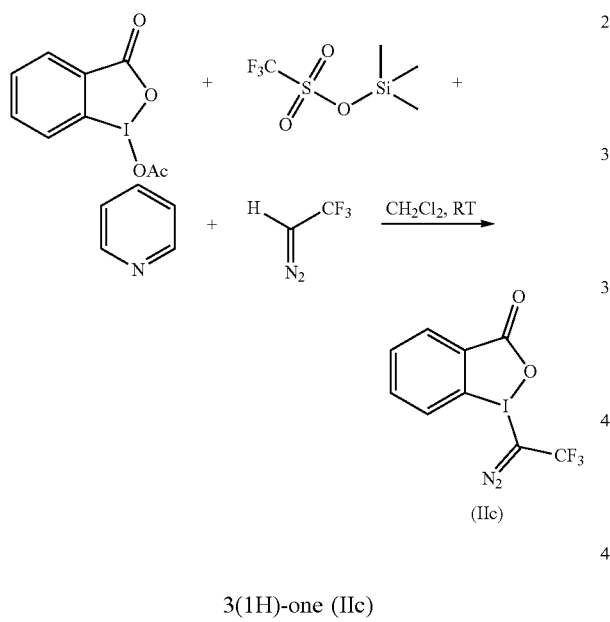

3(1H)-one (IIc)

A solution of 1-acetoxy-1,2-benziodoxol-3(1H)-one (200 mg, 0.65 mmol, 1.0 eq.) in dichloromethane 2.5 mL (0.25 M) was treated with trimethylsilyl trifluoromethanesulfonate (0.12 mL, 0.65 mmol, 1.0 eq.) at room temperature. After 10 min of stirring, a solution of pyridine (0.053 ml, 0.65 mmol, 1.0 eq) in dichloromethane (0.5 ml) was added. The resulted suspension was additionally stirred for 2 h at room temperature. trifluoromethyl diazomethane (0.35M, 2.2 mL, 1.78 mmol, 1.2 eq) was added and the mixture was stirred until a clear yellow solution was obtained. The solution was washed with distilled water (no vigorously shaking!) and dried with anhydrous sodium sulfate. Solvent were removed in a vacuum to afford a yellowish solid. The contained pyridine salt was removed by recrystallization (3 times) from dichloromethane during 12 hours at −30° C. Remove the solvent from the final filtrate and the product was collected as a yellow solid (46 mg, 20% yield), washed with cold diethyl ether (20 mL), dried under high vacuum and stored at −30° C.

$^1$H NMR (400 MHz, DMSO-d$_6$) δ 8.01 (dd, J=7.6, 1.5 Hz, 1H), 7.95 (ddd, J=8.7, 7.1, 1.6 Hz, 1H), 7.83 (d, J=8.0 Hz, 1H), 7.70 (t, J=7.5 Hz, 1H); $^{13}$C NMR (126 MHz, DMSO) δ 168.51, 135.07, 131.73, 131.60, 130.91, 129.55 (q, J=226.80), 126.70, 120.81.

Example 6: Preparation of (1-diazo-2-benzyloxy-2-oxoethyl)(2-(2-benzyloxy-2-oxoethoxyl)carbonyl-phenyl)iodonium Trifluoromethanesulfonate (If)

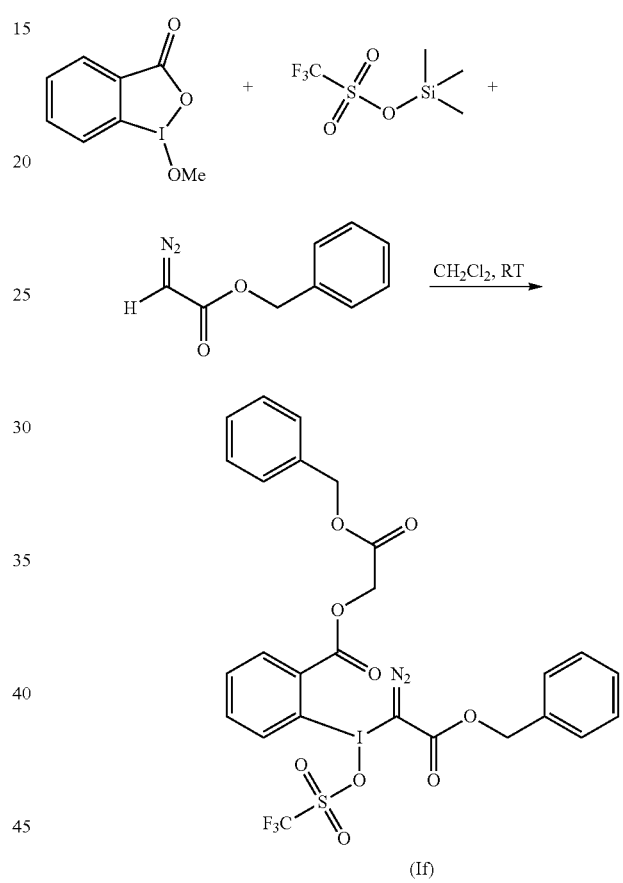

A solution of 1-methoxy-1,2-benziodoxol-3(1H)-one (180 mg, 0.65 mmol, 1.0 eq.) in dichloromethane (2.5 mL, 0.25 M) was treated with trimethylsilyl trifluoromethanesulfonate (0.12 mL, 0.65 mmol, 1.0 eq.) at room temperature. Then benzyl diazoacetate (0.22 mL, 1.43 mmol, 2.2 eq) was added dropwise which accompanied by release of N$_2$ and the reaction mixture was stirred for at room temperature until a clear yellow solution was obtained. Solvent was removed under vacuum and the crude was recrystallized from a mixture of diethyl ether/dichloromethane (5:1) during 12 hours at −30° C. The product was collected by filtration, washed with cold diethyl ether (200 mL), dried under high vacuum and stored at −30° C. Yellow solid (351 mg, 75%).

$^1$H NMR (400 MHz, Acetonitrile-d$_3$) δ 8.41 (dd, J=7.6, 1.7 Hz, 1H), 8.03 (dd, J=8.4, 1.2 Hz, 1H), 7.97 (ddd, J=8.4, 7.1, 1.7 Hz, 1H), 7.90 (td, J=7.4, 1.2 Hz, 1H), 7.42-7.35 (m, 10H), 5.32 (s, 2H), 5.25 (s, 2H), 5.12 (s, 2H); $^{13}$C NMR (101 MHz, Acetonitrile-d$_3$); $^{19}$F NMR (376 MHz, Acetonitrile-d$_3$): δ −79.39.

Example 7: Preparation of (1-diazo-2-tert-butoxy-2-oxoethyl)(2-(2-tert-butoxy-2-oxoethoxyl)carbonylphenyl)iodonium Trifluoromethanesulfonate (Ig)

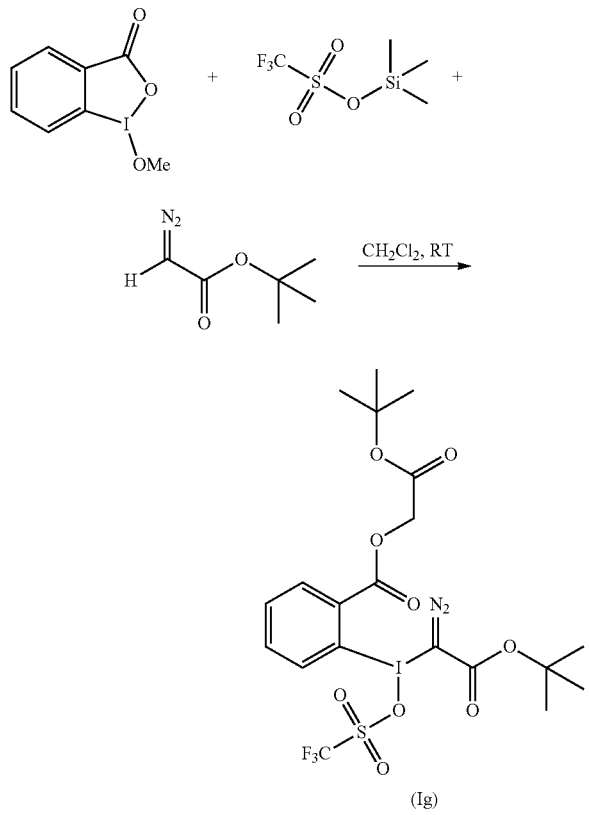

A solution of 1-methoxy-1,2-benziodoxol-3(1H)-one (180 mg, 0.65 mmol, 1.0 eq.) in dichloromethane (2.5 mL, 0.25 M) was treated with trimethylsilyl trifluoromethanesulfonate (0.12 mL, 0.65 mmol, 1.0 eq.) at room temperature. Then t-butyl diazoacetate (0.20 mL, 1.43 mmol, 2.2 eq) was added dropwise which accompanied by release of N$_2$ and the reaction mixture was stirred for at room temperature until a clear yellow solution was obtained. Solvent was removed under vacuum and the crude was recrystallized from a mixture of diethyl ether/dichloromethane (5:1) during 12 hours at −30° C. The product was collected by filtration, washed with cold diethyl ether (200 mL), dried under high vacuum and stored at −30° C. Yellow solid (279 mg, 66%).

$^1$H NMR (400 MHz, Acetonitrile-d$_3$) δ 8.43-8.39 (m, 1H), 8.02 (dd, J=3.6, 0.9 Hz, 2H), 7.91 (ddd, J=7.6, 4.7, 3.5 Hz, 1H), 4.95 (s, 2H), 1.49 (s, 9H), 1.48 (s, 9H); $^{13}$C NMR (101 MHz, Acetonitrile-d$_3$); $^{19}$F NMR (376 MHz, Acetonitrile-d$_3$): δ −79.39

Example 8: Preparation of (1-diazo-2-ethoxy-2-oxoethyl)(2-(2-ethoxy-2-oxoethoxy)carbonylphenyl)iodonium Hexafluorophosphate (Ih)

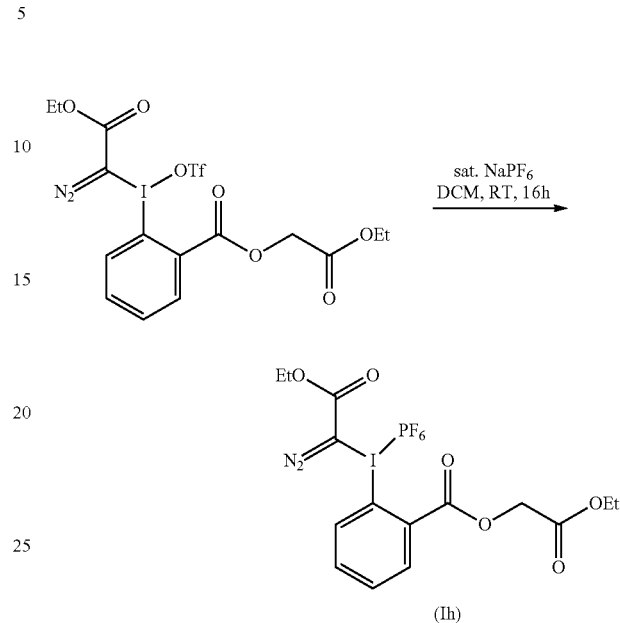

2.0 mL solution of a saturated aqueous solution of NaPF$_6$ was added to a solution of 1.0 mmol of the compound of formula (Id) in 2.0 mL DCM. The resulting biphasic mixture was stirred at room temperature for 16 h until the phases were separated and the aqueous layer extracted with a further three portions of DCM. The combined organic fractions were dried over anhydrous MgSO$_4$ and concentrated in vacuo to give the corresponding PF$_6$ salt as a yellow solid (456 mg, 77%).

$^1$H NMR (400 MHz, CDCl$_3$) δ 8.39 (dd, J=7.7, 1.6 Hz, 1H), 8.03-7.97 (m, 1H), 7.88-7.78 (m, 2H), 5.02 (s, 2H), 4.39-4.22 (m, 4H), 1.33-1.27 (m, 6H); $^{13}$C NMR (101 MHz, CDCl$_3$) δ 169.52, 166.03, 161.14, 138.96, 133.85, 132.39, 128.37, 124.87, 114.93, 64.78, 64.08, 62.53, 14.24, 14.15; $^{19}$F NMR (376 MHz, CDCl$_3$): δ −71.83 (d, J=714.4); $^{31}$P NMR (162 MHz, CDCl$_3$) δ 141.43 (hept, J=712.8).

Example 9: Preparation of (1-diazo-2-ethoxy-2-oxoethyl)(2-(2-ethoxy-2-oxoethoxy)carbonylphenyl)iodonium Tetrafluoroborate (Ii)

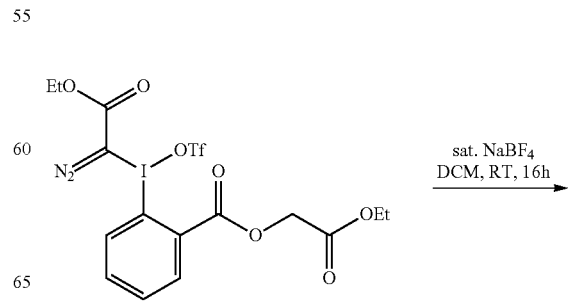

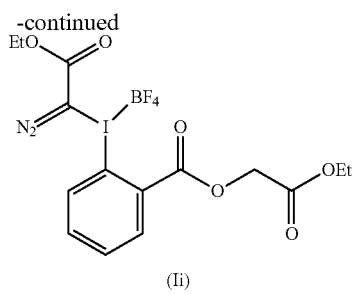

(Ii)

2.0 mL solution of a saturated aqueous solution of NaBF$_4$ was added to a solution of 1.0 mmol of the compound of formula (Id) in 2.0 mL DCM. The resulting biphasic mixture was stirred at room temperature for 16 h until the phases were separated and the aqueous layer extracted with a further three portions of DCM. The combined organic fractions were dried over anhydrous MgSO$_4$ and concentrated in vacuo to give the corresponding BF$_4$ salt as a yellow solid (187 mg, 35%).

$^1$H NMR (400 MHz, CDCl$_3$) δ 8.40 (dd, J=7.7, 1.6 Hz, 1H), 7.95 (dd, J=7.2, 1.6 Hz, 1H), 7.85 (dd, J=8.3, 0.8 Hz, 1H), 7.81 (td, J=7.6, 1.0 Hz, 1H), 5.04 (s, 2H), 4.39-4.25 (m, 4H), 1.37-1.28 (m, 6H); $^{13}$C NMR (101 MHz, CDCl$_3$) δ 169.41, 165.95, 161.30, 138.37, 133.71, 132.13, 128.75, 125.50, 115.82, 64.63, 64.01, 62.57, 14.37, 14.22; $^{19}$F NMR (376 MHz, CDCl$_3$) δ −149.84 (d, J=18.8); $^{11}$B NMR (128 MHz, CDCl$_3$) δ −1.22.

Example 10: Preparation of 1-(1-diazo-2-oxo-2-phenylethyl)-1,2-benziodoxol-3(1H)-one (IId)

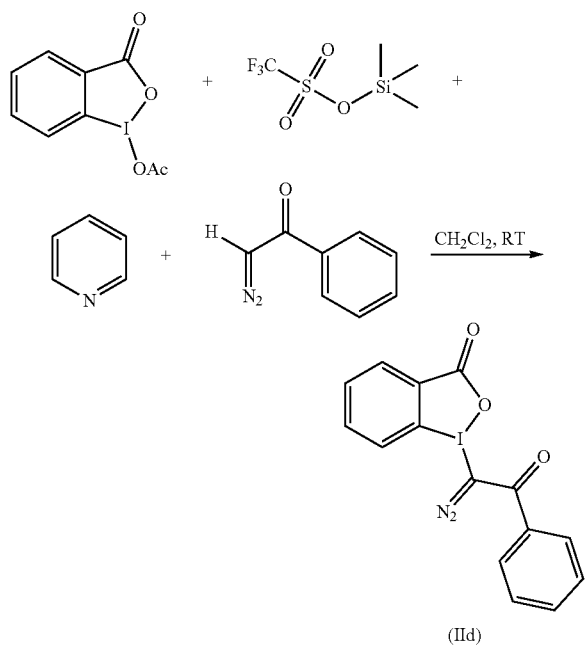

(IId)

A solution of 1-acetoxy-1,2-benziodoxol-3(1H)-one (200 mg, 0.65 mmol, 1.0 eq.) in dichloromethane 2.5 mL (0.25 M) was treated with trimethylsilyl trifluoromethanesulfonate (0.12 mL, 0.65 mmol, 1.0 eq.) at room temperature. After 10 min of stirring, a solution of pyridine (0.053 ml, 0.65 mmol, 1.0 eq) in dichloromethane (0.5 ml) was added. The resulted suspension was additionally stirred for 2 h at room temperature. α-diazoacetophenone in 0.5 mL DCM solution (114 mg, 0.76 mmol, 1.2 eq) was added and the mixture was stirred until a clear yellow solution was obtained. The solution was washed with distilled water and dried with anhydrous sodium sulfate. Solvent was removed in a vacuum to afford a yellowish solid. The contained pyridine salt was removed by recrystallization (3 times) from dichloromethane during 12 hours at −30° C. Remove the solvent from the final filtrate and the product was collected as a yellow solid (73 mg, 29% yield), washed with cold diethyl ether (20 mL), dried under high vacuum and stored at −30° C.

$^1$H NMR (400 MHz, Chloroform-d) δ 8.43-8.37 (m, 1H), 7.74 (ddd, J=5.9, 3.5, 1.9 Hz, 4H), 7.66-7.59 (m, 2H), 7.53 (dd, J=8.3, 6.9 Hz, 2H); $^{13}$C NMR (101 MHz, Chloroform-d) δ 185.69, 167.00, 134.89, 133.35, 133.22, 132.03, 131.50, 129.19, 127.67, 125.00.

Example 11: Preparation of 1-(1-diazo-2-oxo-2-(N,N-diethylamine)ethyl)-1,2-benziodoxol-3(1H)-one (IIe)

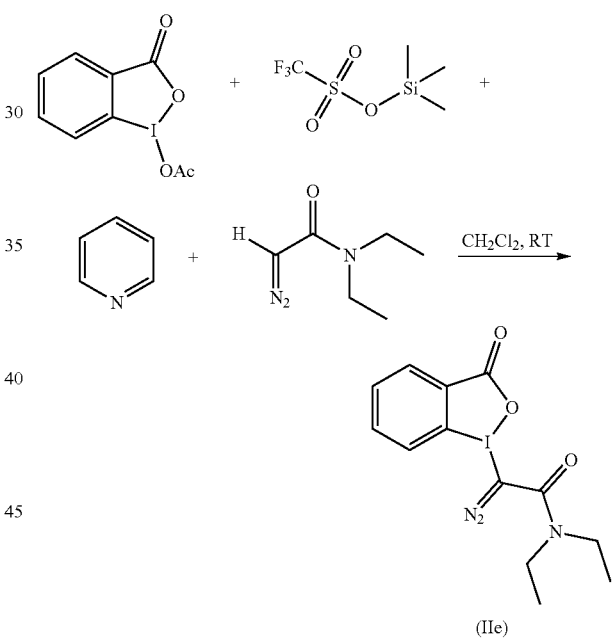

(IIe)

A solution of 1-acetoxy-1,2-benziodoxol-3(1H)-one (200 mg, 0.65 mmol, 1.0 eq.) in dichloromethane 2.5 mL (0.25 M) was treated with trimethylsilyl trifluoromethanesulfonate (0.12 mL, 0.65 mmol, 1.0 eq.) at room temperature. After 10 min of stirring, a solution of pyridine (0.053 ml, 0.65 mmol, 1.0 eq) in dichloromethane (0.5 ml) was added. The resulted suspension was additionally stirred for 2 h at room temperature. 2-diazo-N,N-diethylacetamide in 0.5 mL DCM solution (107 mg, 0.76 mmol, 1.2 eq) was added and the mixture was stirred until a clear yellow solution was obtained. The solution was washed with distilled water (no vigorously shaking!) and dried with anhydrous sodium sulfate. Solvent were removed in a vacuum to afford a yellowish solid. The contained pyridine salt was removed by recrystallization (3 times) from dichloromethane during 12 hours at −30° C. Remove the solvent from the final filtrate and the product was collected as a yellow solid (68 mg, 27% yield), washed with cold diethyl ether (20 mL), dried under high vacuum and stored at −30° C.

$^1$H NMR (400 MHz, DMSO-d$_6$) δ 8.09 (dd, J=7.4, 1.3 Hz, 1H), 7.87-7.79 (m, 2H), 7.74 (ddd, J=7.4, 6.4, 1.7 Hz, 1H), 3.39 (q, J=7.0 Hz, 4H), 1.11 (t, J=7.0 Hz, 6H); $^{13}$C NMR (101 MHz, DMSO) δ 166.61, 160.86, 134.61, 132.74, 131.67, 130.98, 127.45, 116.62, 42.19, 13.40.

Example 12: Preparation of 1-(1-diazo-1-ethoxysulfonylmethyl)-1,2-benziodoxol-3(1H)-one (IIf)

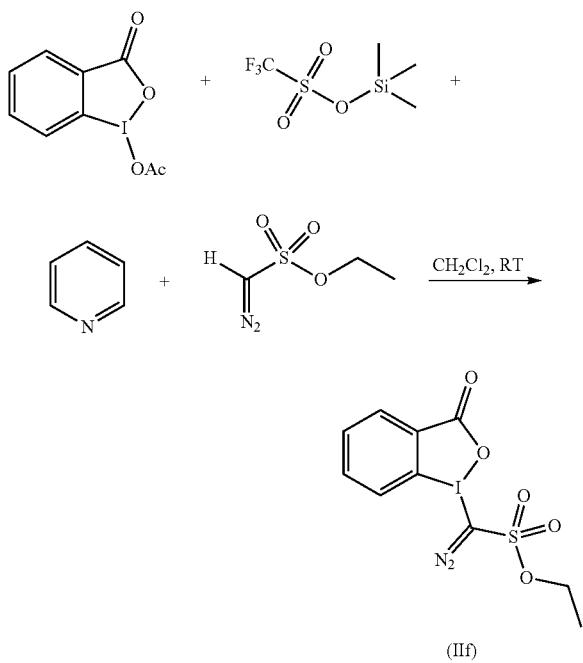

(IIf)

A solution of 1-acetoxy-1,2-benziodoxol-3(1H)-one (200 mg, 0.65 mmol, 1.0 eq.) in dichloromethane 2.5 mL (0.25 M) was treated with trimethylsilyl trifluoromethanesulfonate (0.12 mL, 0.65 mmol, 1.0 eq.) at room temperature. After 10 min of stirring, a solution of pyridine (0.053 ml, 0.65 mmol, 1.0 eq) in dichloromethane (0.5 ml) was added. The resulted suspension was additionally stirred for 2 h at room temperature. Ethyl diazomethanesulfonate in 0.5 mL DCM solution (114 mg, 0.76 mmol, 1.2 eq) was added and the mixture was stirred until a clear yellow solution was obtained. The solution was washed with distilled water (no vigorously shaking!) and dried with anhydrous sodium sulfate. Solvent were removed in a vacuum to afford a yellowish solid. The contained pyridine salt was removed by recrystallization (3 times) from dichloromethane during 12 hours at −30° C. Remove the solvent from the final filtrate and the product was collected as a yellow solid (79 mg, 31% yield), washed with cold diethyl ether (20 mL), dried under high vacuum and stored at −30° C.

$^1$H NMR (400 MHz, DMSO-d$_6$) δ 8.10 (dd, J=7.5, 1.5 Hz, 1H), 7.98-7.90 (m, 2H), 7.83-7.79 (m, 1H), 4.41 (q, J=7.0 Hz, 2H), 1.32 (t, J=7.0 Hz, 3H); $^{13}$C NMR (101 MHz, DMSO) δ 167.42, 140.93, 135.12, 131.62, 130.94, 127.85, 126.69, 69.79, 14.89.

Example 13: Preparation of 1-(1-diazo-1-cianylmethyl)-1,3-dihydro-3,3-dimethyl-1,2-benziodoxole (IIg)

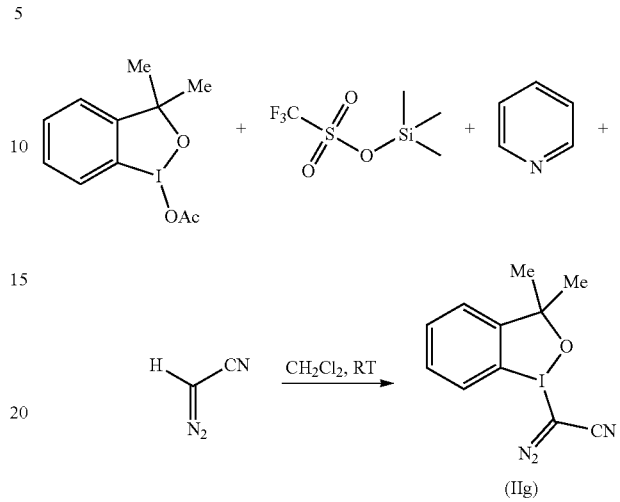

(IIg)

A solution of 1-acetoxy-1,2-benziodoxol-3(1H)-one (180 mg, 0.65 mmol, 1.0 eq.) in dichloromethane 2.5 mL (0.25 M) was treated with trimethylsilyl trifluoromethanesulfonate (0.12 mL, 0.65 mmol, 1.0 eq.) at room temperature. After 10 min of stirring, a solution of pyridine (0.053 ml, 0.65 mmol, 1.0 eq) in dichloromethane (0.5 ml) was added. The resulted suspension was additionally stirred for 2 h at room temperature. 2-Diazoacetonitrile in DCM solution (3.0 mL, 0.76 mmol, 1.2 eq) was added and the mixture was stirred until a clear yellow solution was obtained. The solution was washed with distilled water (no vigorously shaking!) and dried with anhydrous sodium sulfate. Solvent were removed in a vacuum and the residue was purified by flash chromatography (DCM:EA=5:1 as eluent) to afford a yellowish oil (38 mg, 18% yield). The product was not stable at room temperature and should be stored at −30° C.

$^1$H NMR (300 MHz, Chloroform-d) δ 7.65-7.51 (m, 3H), 7.37-7.30 (m, 1H), 1.50 (s, 6H); $^{13}$C NMR (75 MHz, Chloroform-d) δ 149.06, 131.13, 130.35, 127.57, 126.39, 113.45, 111.65, 79.33, 30.68.

Example 14: Diazomethylation Reactions

General Procedure A:

To an oven-dried 8.0 ml tube equipped with a magnetic stir bar was added the compound of formula (I) or of formula (II) as described in Table 1 below (0.13 mmol, 1.3 equiv.), NaHCO$_3$ (25.2 mg, 0.3 mmol, 3.0 equiv.) and Ru(bpy)$_3$(PF$_6$)$_2$ (0.8 mg, 0.001 mmol, 0.01 equiv.). The tube was sealed with septum and degassed 3 times with Argon. The substrate of the reaction incorporating an aromatic moiety (as described in Table 1) (0.1 mmol, 1.0 equiv.) was dissolved in 0.5 ml degassed MeCN and added via a syringe, the resulting mixture was stirred under irradiation of white LED for 2 h. The reaction mixture was diluted with 3.0 ml DCM, followed by addition of 3.0 g silica gel. The solvent was removed under vacuum and the resulting solid was purified by flash chromatography (FC) on silica gel column to afford the product indicated in Table 1 below.

TABLE 1

| Entry | Substrate | Compound of formula (I) or (II) | Product | Yield (%) |
|---|---|---|---|---|
| 1 | p-xylene | (Id) | | 65 |
| 2[1] | p-xylene | (IIa) | 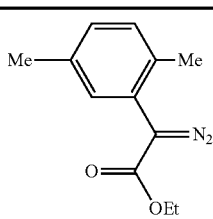 | 20 |
| 3[1] | p-xylene | (IIb) | | 14 |
| 4 | p-xylene | (Ie) | 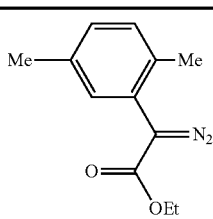 | 75 |

[1]10 mol % Zn(OTf)$_2$ was also added to the reaction mixture.

General Procedure B:

To an oven-dried 8.0 ml tube equipped with a magnetic stir bar was added compound (Id) (119.2 mg, 0.2 mmol, 1.0 equiv.), NaHCO$_3$ (50.4 mg, 0.6 mmol, 3.0 equiv.) and Ru(bpy)$_3$(PF$_6$)$_2$ (1.6 mg, 0.002 mmol, 0.01 equiv.). The tube was sealed with septum and degassed 3 times with Argon. The substrate of the reaction incorporating an aromatic moiety (as described in Table 2) (0.4 mmol, 2.0 equiv.) was dissolved in 2.0 ml degassed acetonitrile and added via a syringe, the resulting mixture was stirred at room temperature adjacent to a 3.45 W white LED. After complete conversion of the diazomethylator reagent (usually 2 h), the reaction mixture was passed through a short plug of silica gel, washed with ethyl acetate. The solvent was removed under vacuum and the residue was purified by column chromatography to afford the product indicated in Table 2 below.

| Entry | Substrate | Product | Yield (%) |
|---|---|---|---|
| 1[1] | 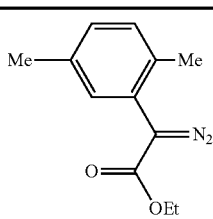 | 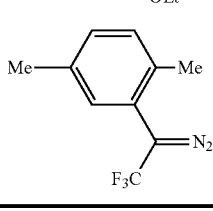 | 52 |
| 2 |  | 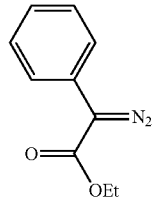 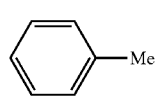 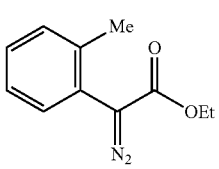 | 62 (o:m:p = 30:1:1) |
| 3 | 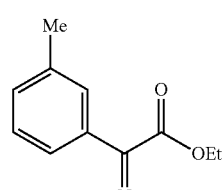 | 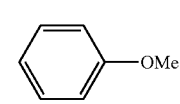 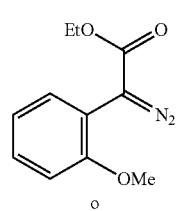 | 57 (o:p = 2:1) |
| 4 | 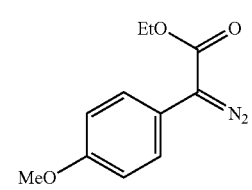 | 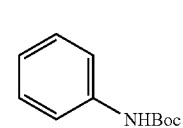 [SMILES: CC(C)(C)OC(=O)Nc1ccccc1] | 51 |

-continued

| Entry | Substrate | Product | Yield (%) |
|---|---|---|---|
| 5 | iodobenzene | o, m, p isomers of ethyl 2-diazo-2-(iodophenyl)acetate | 52 (o:m:p = 18:1:1) |
| 6 | phenyl acetate | o, m, p isomers of ethyl 2-(acetoxyphenyl)-2-diazoacetate | 40 (o:m:p = 3:1:1) |
| 7 | methyl benzoate | o, m, p isomers of ethyl 2-diazo-2-(methoxycarbonylphenyl)acetate | 43 (o:m:p = 2:1:1) |
| 8 | 4-tert-butyltoluene | a, b isomers | 71 (a:b = 9:1) |

-continued
| Entry | Substrate | Product | | Yield (%) |
|---|---|---|---|---|
| 9 | 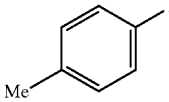 | 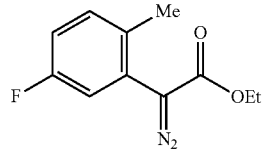<br>a | 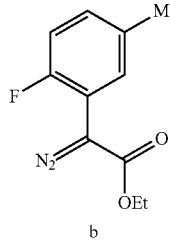<br>b | 37 (a:b = 7:1) |
| 10 | 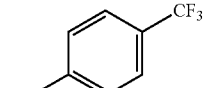 | 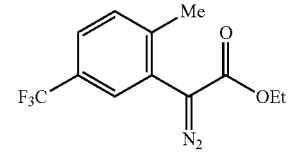<br>a | 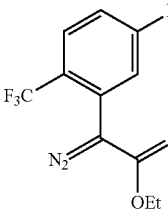<br>b | 30 (a:b = 25:1) |
| 11 | 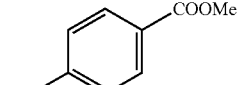 | 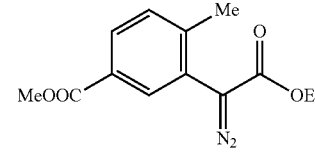<br>a | 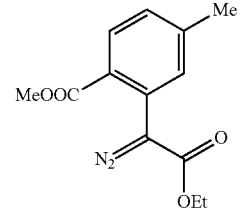<br>b | 41 (a:b = 10:1) |
| 12 | 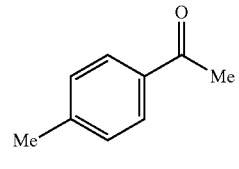 | 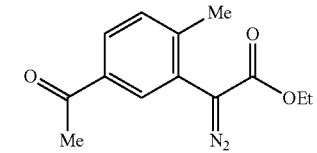<br>a | 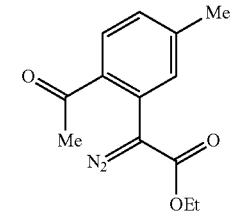<br>b | 34 (a:b = 14:1) |
| 13 | 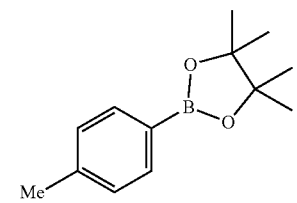 [SMILES: Cc1ccc(B2OC(C)(C)C(C)(C)O2)cc1] | 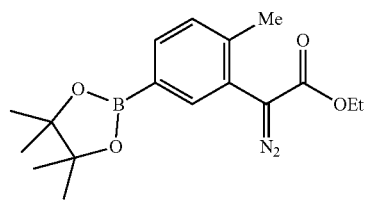<br>a<br>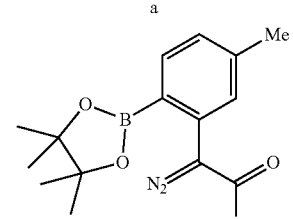<br>b | | 58 (a:b = 9:1) |

-continued
| Entry | Substrate | Product | | Yield (%) |
|---|---|---|---|---|
| 14 | 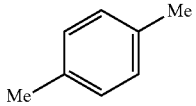 | 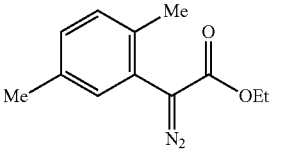 | | 73 |
| 15 | 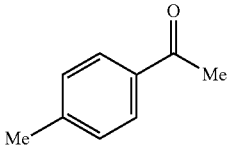 | 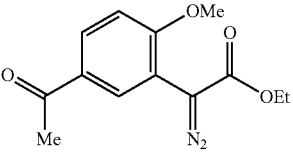 | | 18 |
| 16 | 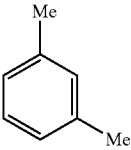 | 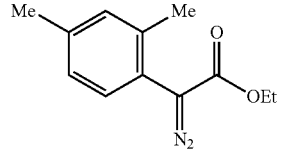 a | 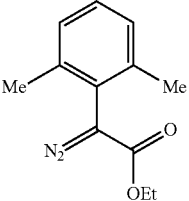 b | 78 (a:b = 2:1) |
| 17[2] | 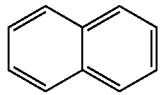 | 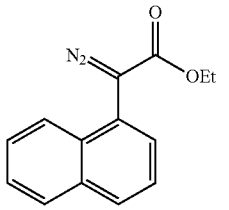 a | 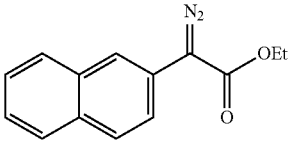 b | 65 (a:b = 20:1) |
| 18 | 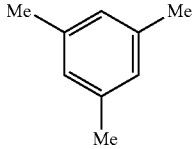 | 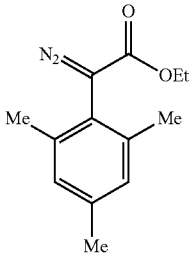 | | 91 |
| 19 | 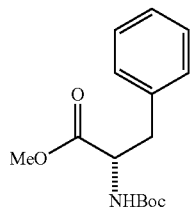 [SMILES: COC(=O)[C@H](Cc1ccccc1)NC(=O)OC(C)(C)C] | 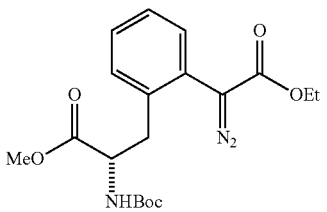 | | 28 |

-continued
| Entry | Substrate | Product | Yield (%) |
|---|---|---|---|
| 20[3] | 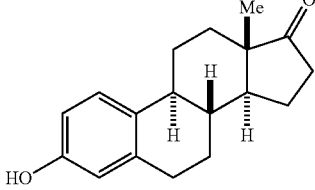 | 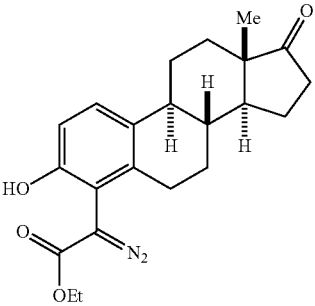 | 30 |
| 21[3] | 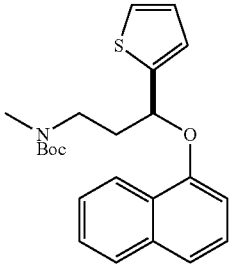 [SMILES: CN(CC[C@H](Oc1cccc2ccccc12)c1cccs1)C(=O)OC(C)(C)C] | 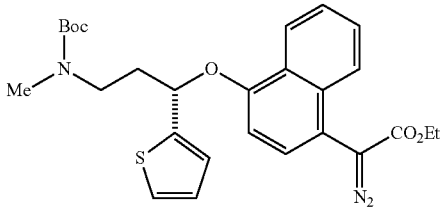 | 45 |
| 22[3] | 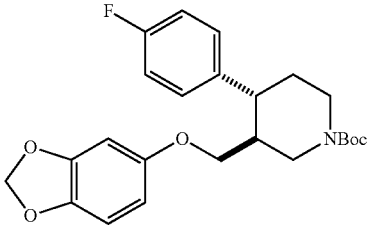 | 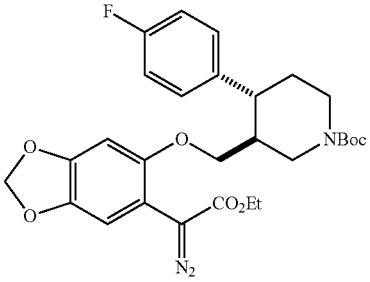 | 35 |
| 23 | 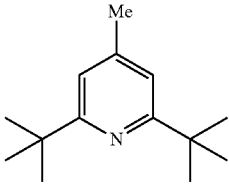 | 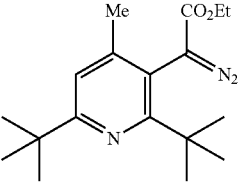 | 82 |
| 24 | 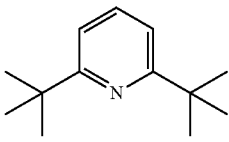 | 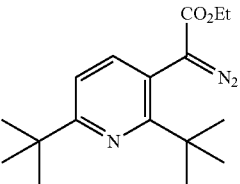 | 56 |
[1] 10.0 equiv. benzene was used.
[2] 2,6-Di-tBu-pyridine was used as base instead of NaHCO$_3$.
[3] catalyst loading was reduced to 0.1 mol % Ru(bpy)$_3$(PF6)$_2$ (0.16 mg, 0.0002 mmol).

General Procedure C:

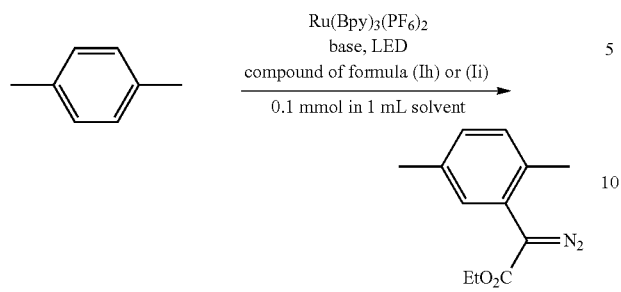

To an oven-dried 8.0 ml tube equipped with a magnetic stir bar was added compound the compound of formula (I) as indicated in the Table 3, the base as indicated in Table 3 below and Ru(bpy)$_3$(PF$_6$)$_2$ (1 mol %). The tube was sealed with septum and degassed 3 times with Argon. p-xylene (amount indicated in Table 3) was dissolved in 1.0 ml degassed solvent (see Table 3) and added via a syringe, the resulting mixture was stirred at room temperature adjacent to a LED. After a certain amount of time, the reaction mixture was evaporated and analyzed by $^1$H NMR. Table 3 shows the conditions and NMR-measured yields for the diazomethylated p-xylene product.

TABLE 3

| Compound of formula (I) | Amount of p-xylene (equiv.) | Amount of (I) (equiv.) | LED colour | Reaction time (h) | Solvent | Base | Yield (%) |
| --- | --- | --- | --- | --- | --- | --- | --- |
| (Ih) | 1 | 1.5 | White | 2 | MeCN | NaHCO$_3$ | 46 |
| (Ih) | 1 | 1.5 | White | 2 | MeCN | 2,6-tBu-Pyridine | 41 |
| (Ih) | 1 | 1.5 | White | 2 | CH$_2$Cl$_2$ | NaHCO$_3$ | Trace |
| (Ih) | 1 | 1.5 | White | 2 | acetone | NaHCO$_3$ | 38 |
| (Ih) | 1 | 1.5 | Blue | 1 | MeCN | NaHCO$_3$ | 35 |
| (Ii) | 1 | 1.5 | White | 2 | MeCN | NaHCO$_3$ | 40 |
| (Ih) | 2 | 1 | White | 2 | MeCN | NaHCO$_3$ | 65 |

PRIOR ART DISCLOSED IN THE APPLICATION

1. Cernak, T.; Dykstra, K. D.; Tyagarajan, S.; Vachal, P.; Krska, S. Chem. Soc. Rev. 2016, 45, 546-576.
2. Ford, A.; Miel, H.; Ring, A.; Slattery C.; Maguire, A. R.; McKervey, M. A. Chem. Rev. 2015, 115, 9981-10080
3. Schnaars, C.; Hennum, M.; Bonge-Hansen, T. J. Org. Chem. 2013, 78, 7488-7497
4. Weiss, R.; Seubert, J.; Hampel, F. Angew. Chem., Int. Ed. 1994, 33 (19), 1952-1953.
5. Li, Y.; Hari, D. P.; Vita, M. V., Waser, J. Angew. Chem. Int. Ed. 2016, 55, 4436-4454

The invention claimed is:
1. A compound of formula (I)

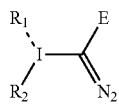

(I)

wherein:
the dotted line means that R$_1$ is attached to the iodine atom through a bond selected from a covalent bond and a ionic bond,
E is a radical selected from the group consisting of the radical of formula -G$_1$, and the radical of formula -G$_2$-G$_3$ wherein:
  G$_1$ and G$_3$ are independently selected from the group consisting of (C$_1$-C$_6$)haloalkyl, (C$_1$-C$_6$)alkyloxycarbonyl, benzyloxycarbonyl, a formyl group (—CHO), (C$_1$-C$_6$)alkylcarbonyl, carboxyl (—COOH), a radical of formula —CONR$_a$R$_b$ wherein R$_a$ and R$_b$ are each independently selected from the group consisting of hydrogen and (C$_1$-C$_6$)alkyl, halogen, nitro, (C$_1$-C$_6$)alkyloxysulfonyl, a radical of formula —P(O)(O(C$_1$-C$_6$)alkyl)$_2$, nitrile and an aromatic ring system comprising from 1 to 2 6-membered aromatic rings, the members being selected from the group consisting of C, CH and N, being at least one member N, and the rings being further optionally substituted at any available position with one or more group selected from halogen, (C$_1$-C$_6$)alkyl, (C$_1$-C$_6$)haloalkyl, (C$_1$-C$_6$)alkyloxy, (C$_1$-C$_6$)alkylcarbonyl, (C$_1$-C$_6$)alkylcarbonyloxy, (C$_1$-C$_6$)alkyloxycarbonyl, nitrile, a formyl group and nitro; and
  G$_2$ is a diradical selected from the group consisting of vinyl (—CH═CH—), carbonyl and an aromatic ring system comprising from 1 to 2 5- to 6-membered aromatic rings, the members being selected from the group consisting of C, CH, O, S and N, and where both the vinyl and the aromatic ring system are further optionally substituted at any available position with one or more groups selected from halogen, (C$_1$-C$_6$)alkyl, (C$_1$-C$_6$)haloalkyl, (C$_1$-C$_6$)alkyloxy, (C$_1$-C$_6$)alkylcarbonyl, (C$_1$-C$_6$)alkylcarbonyloxy, (C$_1$-C$_6$)alkyloxycarbonyl, nitrile, a formyl group and nitro;
R$_1$ is selected from the group consisting of halo, (C$_1$-C$_6$) haloalkylsulfonyloxy, (C$_1$-C$_6$)alkylsulfonyloxy, phenylsulfonyloxy, tolylsulfonyloxy, (C$_1$-C$_6$)alkylcarbonyloxy, hexafluorophosphate, tetrafluoroborate, hexafluoroantimonate, and (C$_1$-C$_6$)haloalkylcarbonyloxy;
R$_2$ is a (C$_6$-C$_{20}$)aryl, optionally substituted at any available position with one or more radicals selected from the group consisting of (C$_1$-C$_6$)alkyl, (C$_1$-C$_6$)alkyloxy, (C$_1$-C$_6$)haloalkyl, (C$_1$-C$_6$)alkylcarbonyl, (C$_1$-C$_6$)alkyloxycarbonyl, and a radical of formula —X—CH$_2$-E' wherein X is a diradical selected from the group consisting of the diradicals of formula —COO—, —C((C$_1$-C$_6$)alkyl)$_2$O—, —SO$_2$—O—, —NR—O—, —B(OR)—O, —S—O—, and —P(O)(OR)—O—, wherein R is H or (C$_1$-C$_6$)alkyl; and E' has the same meaning as E;
or, alternatively,
R$_1$ and R$_2$, together with the iodine atom to which they are attached form a ring in such a way that the compound of formula (I) is a compound of formula (II)

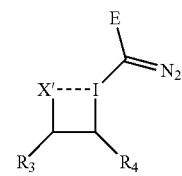

(II)

wherein:

the dotted line means that X' is attached to the iodine atom through a bond selected from a covalent bond and a ionic bond;

X' is a diradical selected from the group consisting of the diradicals of formula —COO—, —C(($C_1$-$C_6$)alkyl)$_2$O—, —SO$_2$—O—, —NR—O—, —B(OR)—O, —S—O—, and —P(O)(OR)—O—, wherein R is H or ($C_1$-$C_6$)alkyl; and $R_3$ and $R_4$, together with the carbon atoms to which they are attached, form an aromatic ring system comprising from 1 to 2 rings, each ring comprising from 5 to 6 members, said members being selected from the group consisting of C, CH, N, NR, being R hydrogen or ($C_1$-$C_6$)alkyl, O and S; and the rings being further optionally substituted with one or more radicals selected from the group consisting of ($C_1$-$C_6$)alkyl, ($C_1$-$C_6$)alkyloxy, ($C_1$-$C_6$)haloalkyl, ($C_1$-$C_6$)alkylcarbonyl, and ($C_1$-$C_6$)alkyloxycarbonyl; and provided that the compound of formula (I) is other than a compound of formula (Ia), or (Ib), or (Ic)

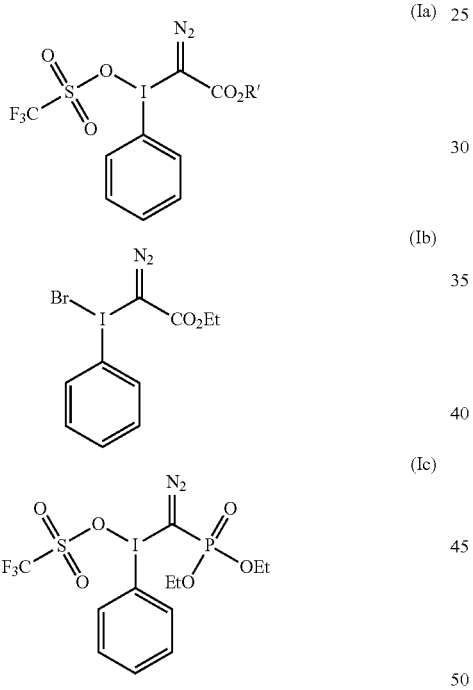

wherein in the compound of formula (Ia) R' is ethyl or tert-butyl.

2. The compound of claim 1, wherein each of E and E' is independently a group of formula -$G_1$ selected from the group consisting of ($C_1$-$C_6$)haloalkyl, ($C_1$-$C_6$)alkyloxycarbonyl, benzyloxycarbonyl, a radical of formula —CONR$_a$R$_b$ wherein R$_a$ and R$_b$ are each independently selected from the group consisting of hydrogen and ($C_1$-$C_6$)alkyl, ($C_1$-$C_6$)alkyloxysulfonyl and nitrile;

or; alternatively, each of E and E' is independently a group of formula -$G_2$-$G_3$, wherein:

$G_3$ is selected from the group consisting of ($C_1$-$C_6$) haloalkyl, ($C_1$-$C_6$)alkyloxycarbonyl, benzyloxycarbonyl, a formyl group (—CHO), ($C_1$-$C_6$)alkylcarbonyl, a radical of formula —CONR$_a$R$_b$ wherein R$_a$ and R$_b$ are each independently selected from the group consisting of hydrogen and ($C_1$-$C_6$)alkyl, ($C_1$-$C_6$)alkyloxysulfonyl, a radical of formula —P(O)(O($C_1$-$C_6$)alkyl)$_2$, phenyl and nitrile; and $G_2$ is a carbonyl group.

3. The compound according to claim 2, wherein each of E and E' is independently selected from the group consisting of trifluoromethyl, ethyloxycarbonyl, tert-butyloxycarbonyl, benzyloxycarbonyl, a radical of formula —CON($C_2H_5$)$_2$, ethyloxysulfonyl, phenylcarbonyl and nitrile.

4. The compound according to claim 1, wherein:

$R_1$ is selected from the group consisting of trifluoromethylsulfonyloxy, hexafluorophosphate and tetrafluoroborate;

$R_2$ is a phenyl optionally substituted at a carbon atom adjacent to the carbon atom of $R_2$ attached to the iodine atom with a radical of formula —X—CH$_2$-E';

wherein X is a diradical selected from the group consisting of the diradicals of formula —COO—, —C(($C_1$-$C_6$)alkyl)$_2$O— and —SO$_2$—O— and E' has the same meaning as E;

or, alternatively;

$R_1$ and $R_2$, together with the iodine atom to which they are attached form a ring in such a way that the compound of formula (I) is a compound of formula (II) wherein X' is a diradical selected from the group consisting of the diradicals of formula —COO—, —C(($C_1$-$C_6$)alkyl)$_2$O— and —SO$_2$—O—; and $R_3$ and $R_4$, together with the carbon atoms to which they are attached, form a phenyl ring.

5. The compound according to claim 4 wherein:

$R_1$ is selected from the group consisting of trifluoromethanesulfonyloxy (CF$_3$—S(O)$_2$—O—), hexafluorophosphate and tetrafluoroborate;

$R_2$ is a phenyl optionally substituted at a carbon atom adjacent to the carbon atom of $R_2$ attached to the iodine atom with a radical of formula —X—CH$_2$-E' wherein X is a diradical of formula —COO—; and E' has the same meaning as E;

or, alternatively;

$R_1$ and $R_2$, together with the iodine atom to which they are attached form a ring in such a way that the compound of formula (I) is a compound of formula (II) wherein X' is a diradical selected from the groups consisting of the diradicals of formula —COO— and —C(CH$_3$)$_2$O—, and $R_3$ and $R_4$, together with the carbon atoms to which they are attached, form a phenyl ring.

6. The compound according to claim 1 that is selected from the compounds of formula (Id), (Ie), (If), (Ig), (Ih) and (Ii)

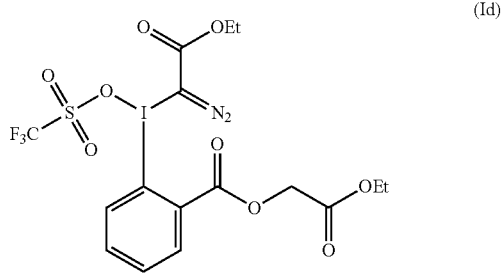

-continued
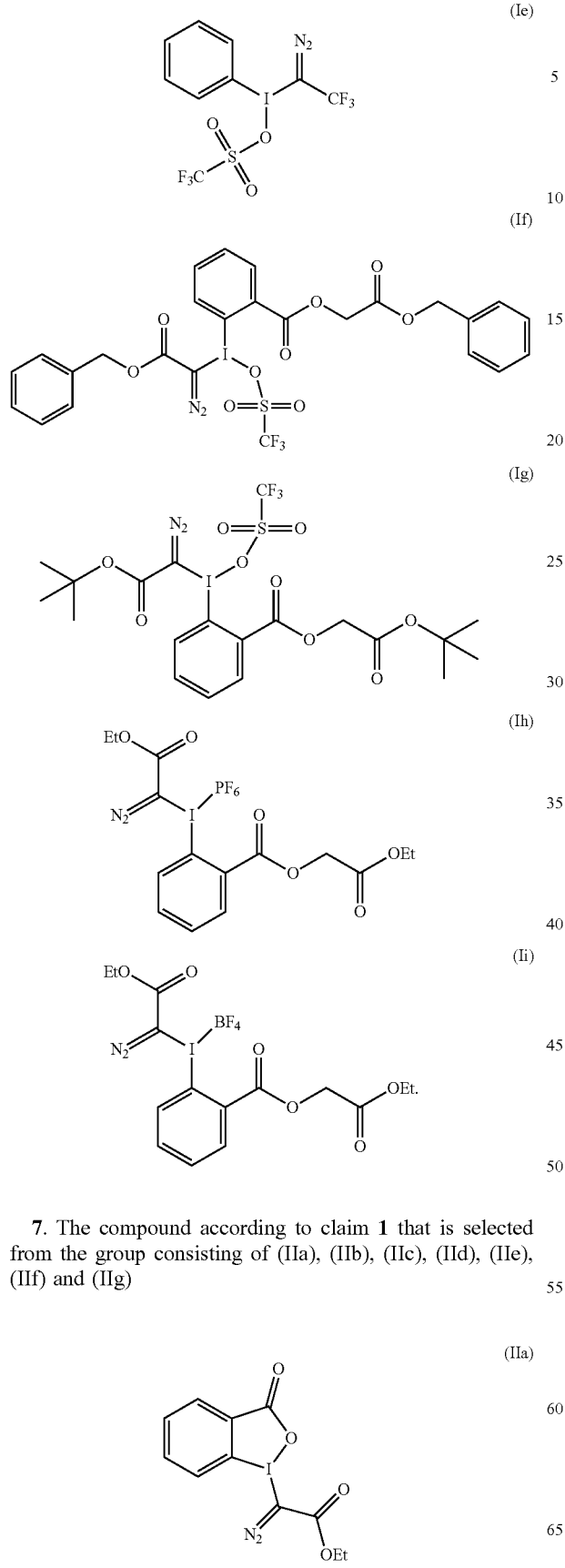
7. The compound according to claim 1 that is selected from the group consisting of (IIa), (IIb), (IIc), (IId), (IIe), (IIf) and (IIg)
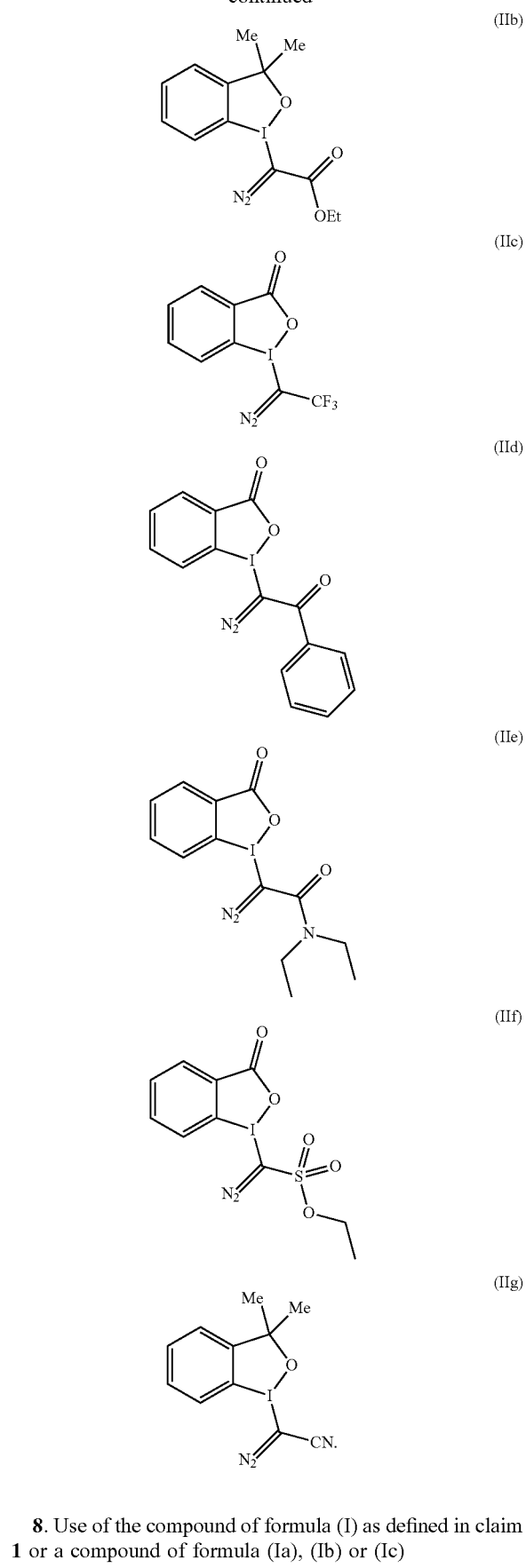
8. Use of the compound of formula (I) as defined in claim 1 or a compound of formula (Ia), (Ib) or (Ic)

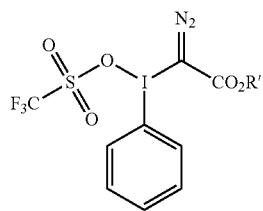
(Ia)

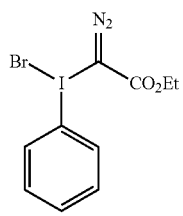
(Ib)

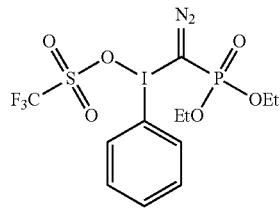
(Ic)

wherein in the compound of formula (Ia) R' is ethyl or tert-butyl; as a reagent for the transfer of a group of formula —C(=N$_2$)(E) to a substrate comprising at least one aromatic or heteroaromatic ring system.

9. A process of preparing a compound comprising a moiety of formula (III)

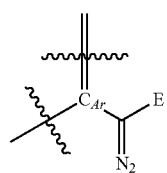
(III)

comprising the step of contacting a compound comprising the moiety of formula (IV)

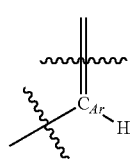
(IV)

with a compound of formula (I) as defined in claim 1 or a compound selected from the compounds of formula (Ia), (Ib) and (Ic)

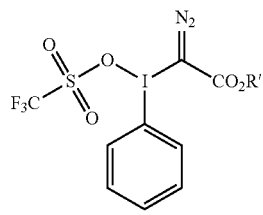
(Ia)

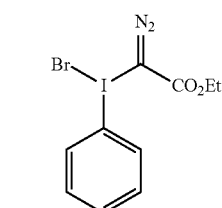
(Ib)

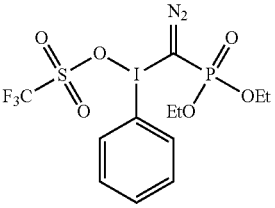
(Ic)

wherein in the compound of formula (Ia) R' is ethyl or tert-butyl, in the presence of a suitable reducing agent and in the presence of a base, wherein, in the compounds comprising the moieties of formula (III) and (IV) C$_{Ar}$ represents a carbon atom comprised in an aromatic or heteroaromatic ring system and wherein the process transforms the moiety of formula (IV) into the moiety of formula (III).

10. The process according to claim 9, wherein the suitable reducing agent is a photoredox catalyst that is used in a catalytically effective amount, and the process is carried out under light irradiation.

11. The process according to claim 10, wherein the suitable reducing agent is a salt of of formula A-Y wherein A is a cation selected from the group consisting of tris-(2,2'-bipyrimidine)ruthenium$^{2+}$, tris-(2,2'-bipyrazine)ruthenium$^{2+}$, tris-(2,2'-bipyridine)ruthenium$^{2+}$, tris-(1,10-phenanthroline)ruthenium$^{2+}$, bis-(2-(2',4'-difluorophenyl)-5-trifluoromethylpyridine)(di-tert-butylbipyridine)iridium$^{+}$, bis-(2-phenylpyridine)(di-tert-butylbipyridine)iridium$^{+}$, and fac-(tris-(2,2'-phenylpyridine))iridium$^{+}$;

and Y is an anion selected from the group consisting of tetrafluoroborate, hexafluorophosphate, chloride, and tetra(pentafluorophenyl)borate.

12. The process according to claim 11, wherein the suitable reducing agent is tris-(2,2'-bipyrimidine)ruthenium$^{2+}$ bis hexafluorophosphate that is used in a catalytically effective amount and the irradiation light is visible light.

13. The process according to claim 9, wherein the base is selected from the group consisting of alkaline bicarbonate salts, alkaline earth bicarbonate salts, and pyridine optionally substituted with one or more (C$_1$-C$_6$)alkyl groups.

14. The process according to claim 9 that is carried out in the presence of a polar aprotic solvent.

15. The process according to claim 9, further comprising the previous step of preparing a compound of formula (I), which comprises contacting a compound of formula (V)

(V)

(V)

wherein $X^2$ is a diradical selected from the group consisting of the diradicals of formula —COO—, —C(($C_1$-$C_6$)alkyl)$_2$O—, —SO$_2$—O—, —NR—O—, —B(OR)—O, —S—O—, and —P(O)(OR)—O—, wherein R is H or ($C_1$-$C_6$)alkyl, with a compound of formula $((C_1$-$C_6)alkyl)_3$Si—$R_1$ (VI)

and a compound of formula $N_2$=CH-E (VII) in the presence of a polar aprotic solvent; and optionally in the presence of a base, wherein:

$R_5$ is a ($C_1$-$C_6$)alkyl, $R_2'$ is a ($C_6$-$C_{20}$)aryl, optionally substituted at any available position with one or more radicals selected from the group consisting of ($C_1$-$C_6$)alkyl, ($C_1$-$C_6$)alkyloxy, ($C_1$-$C_6$)haloalkyl, ($C_1$-$C_6$)alkylcarbonyl, and ($C_1$-$C_6$) alkyloxycarbonyl, or, alternatively, $R_5$ and $R_2'$, together with the atoms to which they are attached, form an aromatic ring system comprising from 1 to 2 rings, each ring comprising from 5 to 6 members, said members being selected from the group consisting of C, CH, N, NR, being R hydrogen or ($C_1$-$C_6$)alkyl, O and S; and the rings being further optionally substituted with one or more radicals selected from the group consisting of ($C_1$-$C_6$)alkyl, ($C_1$-$C_6$)alkyloxy, ($C_1$-$C_6$)haloalkyl, ($C_1$-$C_6$)alkylcarbonyl, and ($C_1$-$C_6$)alkyloxycarbonyl; or, alternatively, $R_5$ and $R_2'$, together with the atoms to which they are attached, form a ($C_6$-$C_{20}$)aryl substituted at any available position with one or more radicals selected from the group consisting of ($C_1$-$C_6$)alkyl, ($C_1$-$C_6$)alkyloxy, ($C_1$-$C_6$)haloalkyl, ($C_1$-$C_6$)alkylcarbonyl, and ($C_1$-$C_6$) alkyloxycarbonyl;

$R_7$ is a ($C_1$-$C_6$)alkyloxycarbonyl or a ($C_1$-$C_6$)alkyloxy; and wherein when in the compound of formula (I) $R_1$ is selected from the group consisting of halo, ($C_1$-$C_6$)haloalkylsulfonyloxy, ($C_1$-$C_6$)alkylsulfonyloxy, phenylsulfonyloxy, tolylsulfonyloxy, ($C_1$-$C_6$)alkylcarbonyloxy, and ($C_1$-$C_6$)haloalkylcarbonyloxy; and $R_2$ is a ($C_6$-$C_{20}$)aryl, optionally substituted at any available position with one or more radicals selected from the group consisting of ($C_1$-$C_6$)alkyl, ($C_1$-$C_6$)alkyloxy, ($C_1$-$C_6$)haloalkyl, ($C_1$-$C_6$)alkylcarbonyl, and ($C_1$-$C_6$)alkyloxycarbonyl; then in the compound of formula (V), $X^2$ is —COO—, $R_5$ is a ($C_1$-$C_6$)alkyl, $R_2'$ is a ($C_6$-$C_{20}$)aryl, optionally substituted at any available position with one or more radicals selected from the group consisting of ($C_1$-$C_6$) alkyl, ($C_1$-$C_6$)alkyloxy, ($C_1$-$C_6$)haloalkyl, ($C_1$-$C_6$)alkylcarbonyl, and ($C_1$-$C_6$)alkyloxycarbonyl, $R_7$ is a ($C_1$-$C_6$)alkyloxycarbonyl; and the molar ratio of the compound of formula (VII) to the compound of formula (V) is comprised from 1:1 to 2:1.

16. The process according to claim 9, further comprising the previous step of preparing a compound of formula (I), which comprises contacting a compound of formula (V)

wherein $X^2$ is a diradical selected from the group consisting of the diradicals of formula —COO—, —C(($C_1$-$C_6$)alkyl)$_2$O—, —SO$_2$—O—, —NR—O—, —B(OR)—O, —S—O—, and —P(O)(OR)—O—, wherein R is H or ($C_1$-$C_6$)alkyl, with a compound of formula $((C_1$-$C_6)alkyl_3SiR_1$ (VI)

and a compound of formula $N_2$=CH-E (VII) in the presence of a polar aprotic solvent; and optionally in the presence of a base, wherein:

$R_5$ is a ($C_1$-$C_6$)alkyl, $R_2'$ is a ($C_6$-$C_{20}$)aryl, optionally substituted at any available position with one or more radicals selected from the group consisting of ($C_1$-$C_6$)alkyl, ($C_1$-$C_6$)alkyloxy, ($C_1$-$C_6$)haloalkyl, ($C_1$-$C_6$)alkyl carbonyl, and ($C_1$-$C_6$) alkyloxycarbonyl, or, alternatively, $R_5$ and $R_2'$, together with the atoms to which they are attached, form an aromatic ring system comprising from 1 to 2 rings, each ring comprising from 5 to 6 members, said members being selected from the group consisting of C, CH, N, NR, being R hydrogen or ($C_1$-$C_6$)alkyl, O and S; and the rings being further optionally substituted with one or more radicals selected from the group consisting of ($C_1$-$C_6$)alkyl, ($C_1$-$C_6$)alkyloxy, ($C_1$-$C_6$)haloalkyl, ($C_1$-$C_6$)alkylcarbonyl, and ($C_1$-$C_6$)alkyloxycarbonyl; or, alternatively, $R_5$ and $R_2'$, together with the atoms to which they are attached, form a ($C_6$-$C_{20}$)aryl substituted at any available position with one or more radicals selected from the group consisting of ($C_1$-$C_6$)alkyl, ($C_1$-$C_6$)alkyloxy, ($C_1$-$C_6$)haloalkyl, ($C_1$-$C_6$)alkylcarbonyl, and ($C_1$-$C_6$) alkyloxycarbonyl;

$R_7$ is a ($C_1$-$C_6$)alkyloxycarbonyl or a ($C_1$-$C_6$)alkyloxy; and wherein when in the compound of formula (I) $R_1$ is selected from the group consisting of halo, ($C_1$-$C_6$)haloalkylsulfonyloxy, ($C_1$-$C_6$)alkylsulfonyloxy, phenylsulfonyloxy, tolylsulfonyloxy, ($C_1$-$C_6$)alkylcarbonyloxy, and ($C_1$-$C_6$)haloalkylcarbonyloxy; and $R_2$ is a ($C_6$-$C_{20}$)aryl substituted at any available position with one or more radicals selected from the group consisting of ($C_1$-$C_6$) alkyl, ($C_1$-$C_6$)alkyloxy, ($C_1$-$C_6$)haloalkyl, ($C_1$-$C_6$)alkylcarbonyl, ($C_1$-$C_6$)alkyloxycarbonyl and the radicals of formula —X—CH$_2$-E', said compound of formula (I) comprising at least one radical of formula —X—CH$_2$-E', then in the compound of formula (V), $R_5$ and $R_2'$, together with the atoms to which they are attached, form a ($C_6$-$C_{20}$)aryl substituted at any available position with one or more radicals selected from the group consisting of ($C_1$-$C_6$)alkyl, ($C_1$-$C_6$)alkyloxy, ($C_1$-$C_6$) haloalkyl, ($C_1$-$C_6$)alkylcarbonyl, and ($C_1$-$C_6$)alkyloxycarbonyl; $R_7$ is a ($C_1$-$C_6$)alkyloxy; and the molar ratio of the compound of formula (VII) to the compound of formula (V) is higher than 2:1.

17. The process according to claim 9, further comprising the previous step of preparing a compound of formula (I), which comprises contacting a compound of formula (V)

(V)

(V)

wherein $X^2$ is a diradical selected from the group consisting of the diradicals of formula —COO—, —C(($C_1$-$C_6$)alkyl)$_2$O—, —SO$_2$—O—, —NR—O—, —B(OR)—O, —S—O—, and —P(O)(OR)—O—, wherein R is H or ($C_1$-$C_6$)alkyl, with a compound of formula (($C_1$-$C_6$)alkyl)$_3$Si—$R_1$ (VI) and a compound of formula $N_2$=CH-E (VII) in the presence of a polar aprotic solvent; and optionally in the presence of a base, wherein:

$R_5$ is a ($C_1$-$C_6$)alkyl, $R_2'$ is a ($C_6$-$C_{20}$)aryl, optionally substituted at any available position with one or more radicals selected from the group consisting of ($C_1$-$C_6$)alkyl, ($C_1$-$C_6$)alkyloxy, ($C_1$-$C_6$)haloalkyl, ($C_1$-$C_6$)alkylcarbonyl, and ($C_1$-$C_6$) alkyloxycarbonyl, or, alternatively, $R_5$ and $R_2'$, together with the atoms to which they are attached, form an aromatic ring system comprising from 1 to 2 rings, each ring comprising from 5 to 6 members, said members being selected from the group consisting of C, CH, N, NR, being R hydrogen or ($C_1$-$C_6$)alkyl, O and S; and the rings being further optionally substituted with one or more radicals selected from the group consisting of ($C_1$-$C_6$)alkyl, ($C_1$-$C_6$)alkyloxy, ($C_1$-$C_6$)haloalkyl, ($C_1$-$C_6$)alkylcarbonyl, and ($C_1$-$C_6$)alkyloxycarbonyl; or, alternatively, $R_5$ and $R_2'$, together with the atoms to which they are attached, form a ($C_6$-$C_{20}$)aryl substituted at any available position with one or more radicals selected from the group consisting of ($C_1$-$C_6$)alkyl, ($C_1$-$C_6$)alkyloxy, ($C_1$-$C_6$)haloalkyl, ($C_1$-$C_6$)alkylcarbonyl, and ($C_1$-$C_6$) alkyloxycarbonyl;

$R_7$ is a ($C_1$-$C_6$)alkyloxycarbonyl or a ($C_1$-$C_6$)alkyloxy; and wherein when in the compound of formula (I) $R_1$ and $R_2$, together with the iodine atom to which they are attached form a ring in such a way that the compound of formula (I) is a compound of formula (II); then the process is carried out in the presence of a base, and in the compound of formula (V), $R_5$ and $R_2'$, together with the atoms to which they are attached, form an aromatic ring system comprising from 1 to 2 rings, each ring comprising from 5 to 6 members, said members being selected from the group consisting of C, CH, N, NR, being R hydrogen or ($C_1$-$C_6$)alkyl, O and S; and the rings being further optionally substituted with one or more radicals selected from the group consisting of ($C_1$-$C_6$)alkyl, ($C_1$-$C_6$)alkyloxy, ($C_1$-$C_6$)haloalkyl, ($C_1$-$C_6$)alkylcarbonyl, and ($C_1$-$C_6$)alkyloxycarbonyl; and $R_7$ is a ($C_1$-$C_6$)alkyloxycarbonyl.

18. The process according to claim 9, further comprising the previous step of preparing a compound of formula (I), which comprises contacting a compound of formula (V)

wherein $X^2$ is a diradical selected from the group consisting of the diradicals of formula —COO—, —C(($C_1$-$C_6$)alkyl)$_2$O—, —SO$_2$—O—, —NR—O—, —B(OR)—O, —S—O—, and —P(O)(OR)—O—, wherein R is H or ($C_1$-$C_6$)alkyl, with a compound of formula (($C_1$-$C_6$)alkyl)$_3$Si—$R_1$ (VI) and a compound of formula $N_2$=CH-E (VII) in the presence of a polar aprotic solvent; and optionally in the presence of a base, wherein:

$R_5$ is a ($C_1$-$C_6$)alkyl, $R_2'$ is a ($C_6$-$C_{20}$)aryl, optionally substituted at any available position with one or more radicals selected from the group consisting of ($C_1$-$C_6$)alkyl, ($C_1$-$C_6$)alkyloxy, ($C_1$-$C_6$)haloalkyl, ($C_1$-$C_6$)alkylcarbonyl, and ($C_1$-$C_6$) alkyloxycarbonyl, or, alternatively, $R_5$ and $R_2'$, together with the atoms to which they are attached, form an aromatic ring system comprising from 1 to 2 rings, each ring comprising from 5 to 6 members, said members being selected from the group consisting of C, CH, N, NR, being R hydrogen or ($C_1$-$C_6$)alkyl, O and S; and the rings being further optionally substituted with one or more radicals selected from the group consisting of ($C_1$-$C_6$)alkyl, ($C_1$-$C_6$)alkyloxy, ($C_1$-$C_6$)haloalkyl, ($C_1$-$C_6$)alkylcarbonyl, and ($C_1$-$C_6$)alkyloxycarbonyl; or, alternatively, $R_5$ and $R_2'$, together with the atoms to which they are attached, form a ($C_6$-$C_{20}$)aryl substituted at any available position with one or more radicals selected from the group consisting of ($C_1$-$C_6$)alkyl, ($C_1$-$C_6$)alkyloxy, ($C_1$-$C_6$)haloalkyl, ($C_1$-$C_6$)alkylcarbonyl, and ($C_1$-$C_6$) alkyloxycarbonyl;

$R_7$ is a ($C_1$-$C_6$)alkyloxycarbonyl or a ($C_1$-$C_6$)alkyloxy; and wherein when in the compound of formula (I) $R_1$ is selected from hexafluorophosphate, hexafluoroantimonate and tetrafluoroborate and $R_2$ is a ($C_6$-$C_{20}$)aryl optionally substituted at any available position with one or more radicals selected from the group consisting of ($C_1$-$C_6$) alkyl, ($C_1$-$C_6$)alkyloxy, ($C_1$-$C_6$)haloalkyl, ($C_1$-$C_6$)alkylcarbonyl, ($C_1$-$C_6$)alkyloxycarbonyl and the radicals of formula —X—CH$_2$-E'; then the product resulting from the processes described in the step (i) or in the step (ii) above is further contacted with an aqueous saturated solution of sodium hexafluorophosphate when $R_1$ is hexafluorophosphate, an aqueous saturated solution of sodium hexafluoroantimonate when $R_1$ is hexafluoroantimonate, or with an aqueous saturated solution of sodium tetrafluoroborate when $R_1$ is tetrafluoroborate.

19. The process according to claim 9, wherein the base is selected from the group consisting of sodium hydrogen carbonate and 2,6-di-tert-butylpyridine.

20. The process according to claim 14 wherein the polar aprotic solvent is acetonitrile.

* * * * *